(12) United States Patent
Aramburu et al.

(10) Patent No.: US 12,583,802 B2
(45) Date of Patent: Mar. 24, 2026

(54) AUTONOMOUS DEVICE FOR IN-FIELD CONVERSION OF BIOMASS INTO BIOCHAR

(71) Applicant: Applied Carbon, Inc., Houston, TX (US)

(72) Inventors: Jason Aramburu, Houston, TX (US); Morgan Williams, Fruita, CO (US)

(73) Assignee: Applied Carbon, Inc., Houston, TX (US)

( * ) Notice: Subject to any disclaimer, the term of this patent is extended or adjusted under 35 U.S.C. 154(b) by 832 days.

(21) Appl. No.: 17/962,887

(22) Filed: Oct. 10, 2022

(65) Prior Publication Data

US 2023/0036555 A1 Feb. 2, 2023

Related U.S. Application Data

(62) Division of application No. 17/353,770, filed on Jun. 21, 2021, now Pat. No. 11,465,948.

(Continued)

(51) Int. Cl.
C05D 9/02 (2006.01)
A01B 3/36 (2006.01)
(Continued)

(52) U.S. Cl.
CPC .................. C05D 9/02 (2013.01); A01B 3/36 (2013.01); A01D 34/008 (2013.01);
(Continued)

(58) Field of Classification Search
CPC ...... C05D 9/02; G05D 1/0217; G05D 1/0094; A01B 3/36; C10B 53/02; C10B 47/44;
(Continued)

(56) References Cited

U.S. PATENT DOCUMENTS 9,155,247 B1 * 10/2015 Force .................. A01D 43/003
2011/0252699 A1 10/2011 Shepard
(Continued)

FOREIGN PATENT DOCUMENTS

CN 209669132 U 11/2019
JP 2004305986 A 11/2004
(Continued)

OTHER PUBLICATIONS

International Search Report and Written Opinion of the International Search Authority in international application No. PCT/US2021/038317, mailed on Oct. 21, 2021.
(Continued)

*Primary Examiner* — Wayne A Langel
(74) *Attorney, Agent, or Firm* — Cognition IP, P.C.; Edward Steakley; Justin White

(57) ABSTRACT

Systems, methods and apparatus for the thermal conversion of biomass into biochar. A mobile platform may be used to maneuver a mobile biochar generation system within a field of biomass. The biomass may be harvested, preprocessed and pyrolyzed. After pyrolyzation, the biochar may be cooled to a predetermined temperature by integrating water and liquid nutrients into the biochar. The system may then control the application of the infused biochar by adjusting a spreading attachment and a plowing attachment.

22 Claims, 32 Drawing Sheets

Related U.S. Application Data

(60) Provisional application No. 63/091,263, filed on Oct. 13, 2020, provisional application No. 63/041,702, filed on Jun. 19, 2020.

(51) Int. Cl.

| | |
|---|---|
| *A01D 34/00* | (2006.01) |
| *A01D 43/00* | (2006.01) |
| *A01D 43/08* | (2006.01) |
| *B01J 19/20* | (2006.01) |
| *C10B 47/44* | (2006.01) |
| *C10B 53/02* | (2006.01) |
| *G05D 1/00* | (2006.01) |
| *A01M 21/04* | (2006.01) |
| *C05C 11/00* | (2006.01) |
| *C10L 5/44* | (2006.01) |
| *F24B 13/04* | (2006.01) |
| *G01N 33/00* | (2006.01) |

(52) U.S. Cl.
CPC ........... *A01D 43/003* (2013.01); *A01D 43/08* (2013.01); *B01J 19/20* (2013.01); *C10B 47/44* (2013.01); *C10B 53/02* (2013.01); *G05D 1/0094* (2013.01); *G05D 1/0217* (2013.01); *A01M 21/04* (2013.01); *C05C 11/00* (2013.01); *C10L 5/445* (2013.01); *F24B 13/04* (2013.01); *G01N 33/0031* (2013.01)

(58) Field of Classification Search
CPC ........ B01J 19/20; A01D 43/08; A01D 34/008; A01D 43/003
See application file for complete search history.

(56) References Cited

U.S. PATENT DOCUMENTS

| | | | |
|---|---|---|---|
| 2012/0193212 A1 | 8/2012 | Taniguro et al. | |
| 2013/0192321 A1 * | 8/2013 | Cheiky | C10L 5/442 |
| | | | 71/25 |
| 2013/0299332 A1 | 11/2013 | Smaidris | |
| 2015/0128672 A1 * | 5/2015 | Shearer | C05G 3/00 |
| | | | 71/24 |
| 2017/0210677 A1 | 7/2017 | Bontchev et al. | |
| 2018/0010043 A1 * | 1/2018 | Archuleta, Jr. | C05G 3/00 |
| 2019/0124819 A1 * | 5/2019 | Madsen | G05D 1/0274 |
| 2019/0129435 A1 * | 5/2019 | Madsen | A01B 69/008 |
| 2019/0330533 A1 | 10/2019 | Olander et al. | |
| 2020/0056098 A1 | 2/2020 | Seidner | |

FOREIGN PATENT DOCUMENTS

| | | | | |
|---|---|---|---|---|
| WO | 2006117005 A1 | 11/2006 | | |
| WO | WO-2012058431 A1 * | 5/2012 | ............. | A01D 43/00 |
| WO | WO-2014016799 A2 * | 1/2014 | ............. | C10B 47/44 |
| WO | WO-2014079572 A1 * | 5/2014 | ............... | C07C 7/08 |

OTHER PUBLICATIONS

Extended European Search Report received in European application No. 21824826.8, mailed on Jun. 7, 2024.

Arteaga, Carols Miranda, Robert Boutin, and Thushara Nanayakkara. "Carbon Sequestration via Autonomous Biochar Processing." (2011).

* cited by examiner

Mobile Biochar Generation
System Controller
305

Pyrolysis System
Control Module
400

Pretreatment System
Control Module
405

Cooling System
Control Module
410

Sensor Analysis
Module
415

Power Module
420

Communication Module
425

LoRa Module
430

BLE Module
435

3GPP Module
440

WIFI Module
445

2600

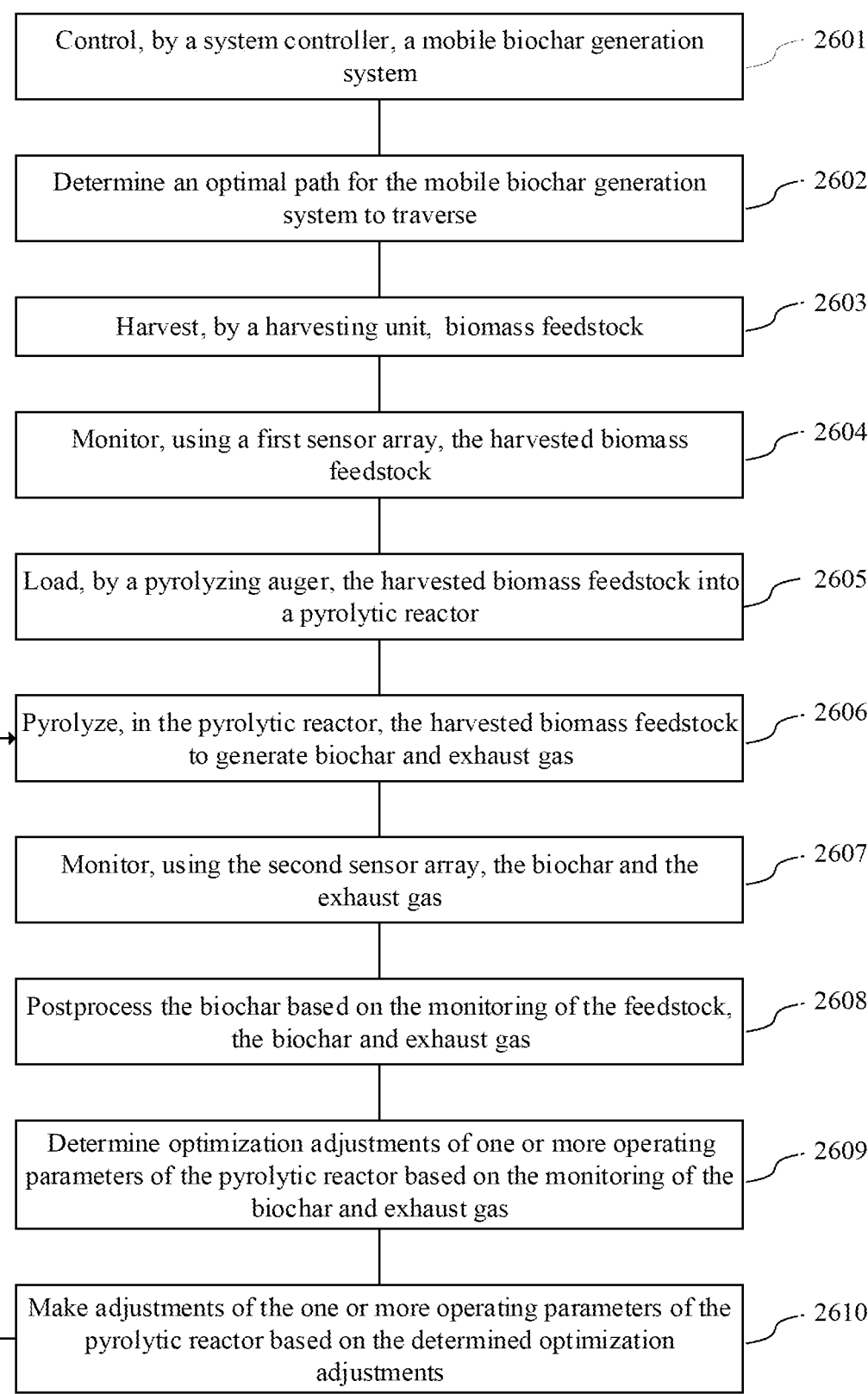

Control, by a system controller, a mobile biochar generation system — 2601

Determine an optimal path for the mobile biochar generation system to traverse — 2602

Harvest, by a harvesting unit, biomass feedstock — 2603

Monitor, using a first sensor array, the harvested biomass feedstock — 2604

Load, by a pyrolyzing auger, the harvested biomass feedstock into a pyrolytic reactor — 2605

Pyrolyze, in the pyrolytic reactor, the harvested biomass feedstock to generate biochar and exhaust gas — 2606

Monitor, using the second sensor array, the biochar and the exhaust gas — 2607

Postprocess the biochar based on the monitoring of the feedstock, the biochar and exhaust gas — 2608

Determine optimization adjustments of one or more operating parameters of the pyrolytic reactor based on the monitoring of the biochar and exhaust gas — 2609

Make adjustments of the one or more operating parameters of the pyrolytic reactor based on the determined optimization adjustments — 2610

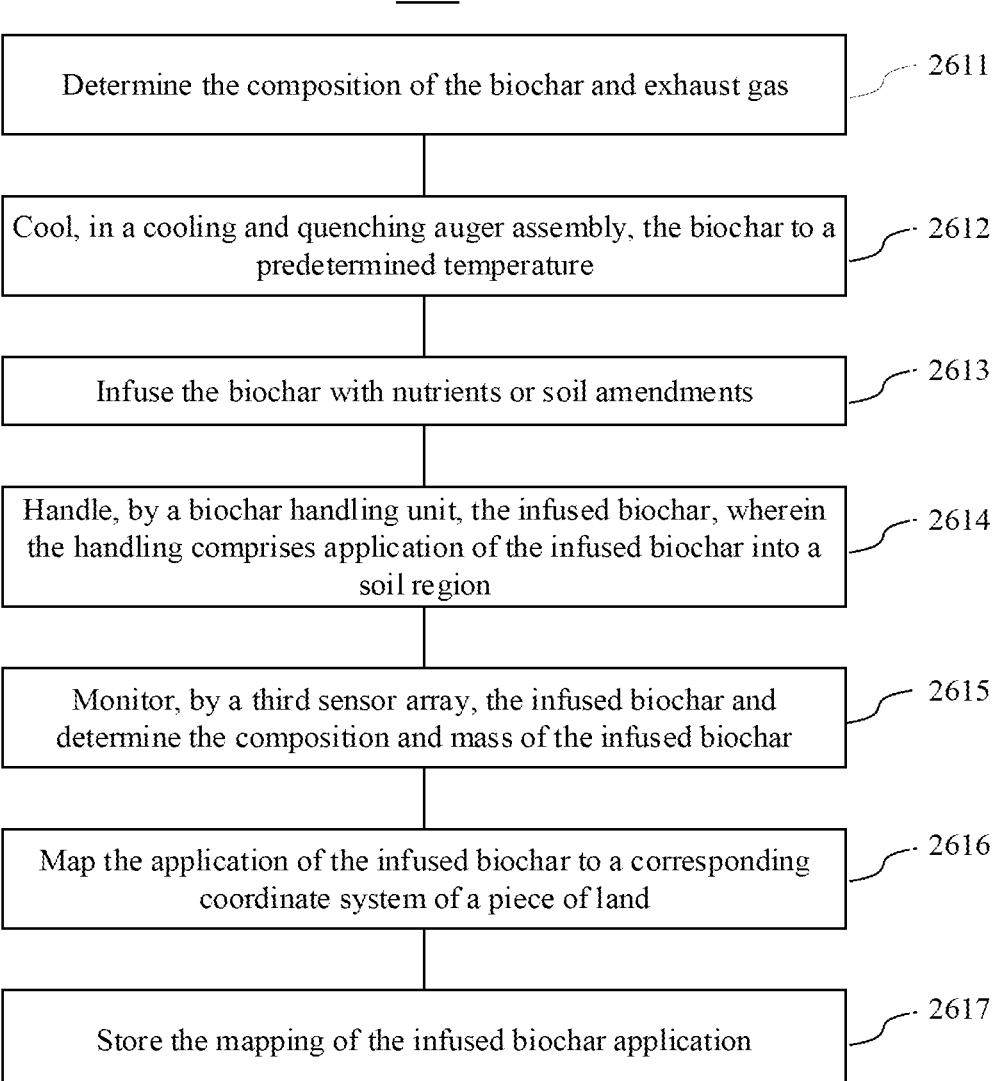

Determine the composition of the biochar and exhaust gas — 2611

Cool, in a cooling and quenching auger assembly, the biochar to a predetermined temperature — 2612

Infuse the biochar with nutrients or soil amendments — 2613

Handle, by a biochar handling unit, the infused biochar, wherein the handling comprises application of the infused biochar into a soil region — 2614

Monitor, by a third sensor array, the infused biochar and determine the composition and mass of the infused biochar — 2615

Map the application of the infused biochar to a corresponding coordinate system of a piece of land — 2616

Store the mapping of the infused biochar application — 2617

FIG. 26B

AUTONOMOUS DEVICE FOR IN-FIELD CONVERSION OF BIOMASS INTO BIOCHAR

CROSS-REFERENCE TO RELATED APPLICATIONS

This application is a divisional of and claims priority to U.S. patent application Ser. No. 17/353,770, filed 21 Jun. 2021, and titled "AUTONOMOUS DEVICE FOR IN-FIELD CONVERSION OF BIOMASS INTO BIOCHAR," which in turn claims the benefit of U.S. Provisional Application No. 63/041,702, filed 19 Jun. 2020, and U.S. Provisional Application No. 63/091,263, filed 13 Oct. 2020, all of which are hereby incorporated by reference in their entireties.

FIELD OF INVENTION

This subject invention relates to robots, preferably an autonomous robot for thermal conversion of biomass into biochar.

BACKGROUND

The thermal conversion of biomass into charcoal or biochar is known as pyrolysis. During pyrolysis, biomass feedstock is heated to temperatures in excess of 300 degrees centigrade under restricted oxygen conditions, resulting in the thermal decomposition of the biomass. Pyrolysis of biomass generates flammable, gaseous byproducts (pyrolysis gas), liquid byproducts (pyrolysis oils) and solid products (biochar). The ratio of each product is determined by the temperature and oxygen concentration of the pyrolysis oven, and the amount of time the biomass feedstock is exposed to pyrolysis conditions (residence time).

Production of biochar is of particular interest to agriculture due to a number of beneficial soil amendment properties. When added to soil, biochar increases carbon concentration, which results in improved water holding capacity, nutrient retention and aeration. Biochar also impacts the chemical composition of the soil by increasing soil pH, and increasing cation exchange capacity. Changes in soil properties as a result of biochar application may increase crop yield and/or reduce input requirements (fertilizer, water etc.).

Biochar is also interesting as a means to sequester atmospheric carbon and reduce the impact of global climate change. When waste biomass is thermally converted to biochar, a significant portion of the carbon content of the feedstock is converted to a mineral form of carbon. In its mineral form, carbon is not readily decomposed. When this mineral carbon is added to soils, it can be safely sequestered for many years. It is estimated that one tonne of biochar is equivalent to more than 3 tons of carbon-dioxide equivalent, based on the molecular weight of carbon dioxide. Large-scale production of biochar from agricultural waste biomass has the potential to sequester vast amounts of atmospheric $CO_2$.

A key challenge associated with scaling up biochar production globally is the availability of biomass waste feedstock in sufficient quantities, and the costs associated with collecting these feedstocks for thermal conversion. Similarly, another challenge is the cost of redistributing the biochar to the soil across many acres of farmland. Finally, the high cost of building a large, centralized, biochar plant is often prohibitive to rapid growth of producers.

SUMMARY

Described herein is an exemplary system and methods of operation an autonomous robot for thermal conversion of biomass into biochar.

In some embodiments, the system may be configured to control a mobile biochar generation system. In some embodiments, an optimal path of a tractor or other transportation unit may be determined. The system may include a harvesting unit, wherein the harvesting unit may be a forage harvester mounted on a tractor. The harvesting unit may be mounted in front of the tractor or between the tractor and a trailer unit which houses a pyrolytic system.

In some embodiments, there may be a plurality of sensor arrays mounted on and inside different components of the system. The plurality of sensor arrays may be used to track and characterize properties of biomass, biochar, exhaust gas and infused biochar.

In some embodiments, biomass may be transferred into a pyrolytic reactor with a pyrolyzing auger. The pyrolytic reactor may comprise a thermally insulated enclosure, one or more heat source, including induction and resistance based heating sources, a portion of the pyrolytic auger and injection ports for gas injection. In some embodiments, the pyrolytic auger may have a hollow shaft with holes along its length where gas and steam may be injected into the reactor.

The pyrolytic reactor may pyrolyze the harvested biomass and generate biochar and exhaust gas. In some embodiments, postprocessing may be performed on the biochar. Post processing may include cooling in a quenching auger, spraying with water, integration of liquid nutrients into the biochar or combination thereof.

In some embodiments, a biochar handling unit may be configured to apply the infused biochar in into a soil region. The biochar handling unit may comprise a spreader unit and a plowing unit to evenly integrate the biochar into the soil.

In some embodiments, the location, amount and density of biochar application may be mapped, saved and analyzed.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein:

FIG. 26A is a flow chart illustrating an exemplary method that may be performed in accordance with some embodiments.

FIG. 26B is a flow chart illustrating an exemplary method that may be performed in accordance with some embodiments.

DETAILED DESCRIPTION

Figure 1:
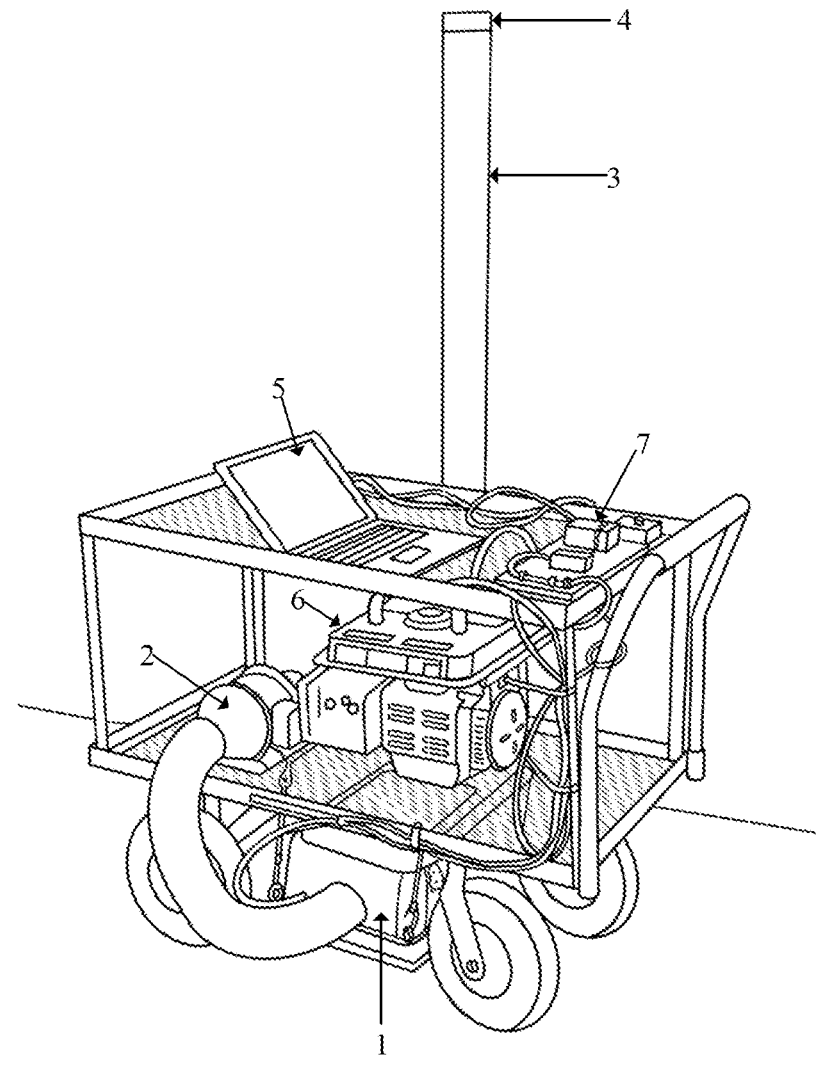
FIG. 1 illustrates an example embodiment of a pyrolysis system in accordance with aspects of the present disclosure.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Disclosed is a mobile robot-based system that converts biomass feedstock into biochar in the field. Unlike centralized biochar production plants, the robot drives across open land or farm fields and converts dry biomass on the soil surface directly into biochar in the field. The robot preferably includes an outdoor mobility platform, a power source, sensors able to detect the boundary of the robot's designated operating area, sensors able to detect obstacles, one or more sensors that can detect the presence and type of biomass, and a mechanism for converting the biomass into biochar. Optionally included are a system for collecting information about soil and plants, and a system for collecting images of plants and soil as well as data for offline analysis of plant/soil health and/or visualization of growth over time.

The mobility platform may include four or six drive wheels each powered by an independent motor controlled by a common microprocessor. In some embodiments, the mobility platform may be a tractor. The tractor may be autonomous, semi-autonomous with human supervision or human operated. The robot is powered by an internal battery which can be charged electrically or via an onboard solar panel. The robot may also be powered by a fuel cell. The robot uses GPS and other sensors to determine its absolute position and its position relative to the boundary of the field in which the robot can travel. GPS and other sensors may also be used as a means to geolocate sequestered biochar carbon for accounting, auditing, and monetization of carbon credits and their derivatives.

The robot uses a number of onboard sensors to identify and avoid obstacles. These sensors include ultrasonic sensors, Lidar, radar, and cameras. The robot may also utilize touch or capacitive sensors along its perimeter to identify obstacles.

The robot uses a number of onboard sensors to navigate within its environment and determine an optimal path. These sensors include lidar, radar, gps, cameras and ultrasonic sensors.

The biomass pyrolysis system includes a heat source capable of reaching temperatures in excess of 250 degrees centigrade. This heat source could be an electric heater, a ceramic heater, a laser, a microwave energy source, infrared heater or a burner capable of combusting a liquid or gaseous fuel such as propane. The biomass pyrolysis system also consists of a thermally-insulated metal or ceramic enclosure that allows biomass to enter and exit but restricts the entry of oxygen. This enclosure may include curtains or flaps to restrict oxygen within the pyrolysis chamber while allowing biomass to freely enter and exit. An onboard system to consolidate, reorient, or compartmentalize field collected biomass within the robot may be used to optimize thermal conversion efficiencies. The Pyrolysis system may also include a chimney for exhaust of gases and combustion products, along with a blower or source of pressurized inert gas to control the amount of oxygen present in the pyrolysis chamber. The pyrolysis system also includes a temperature controller which regulates the intensity of the heat source to achieve and maintain a desired temperature.

The pyrolysis system includes a number of sensors to monitor and optimize the pyrolysis process. These sensors may include temperature sensors, sensors to measure the concentration of gases such as oxygen and carbon dioxide and sensors to measure the speed of the robot to determine biomass residence time.

The pyrolysis system may include a number of actuators to optimize the pyrolysis process including electrically operated augers or wheels to efficiently move biomass through the pyrolysis zone. The pyrolysis system may also include actuators to adjust the height of the enclosure.

The pyrolysis system may include active and passive cooling systems to reduce the temperature of the biochar below combustion temperature. These cooling systems may include blowers, water sprayers, heat sinks, refrigeration systems or peltier coolers to reduce the temperature of the biochar. The cooling system may integrate nutrient laden fluids containing nitrogen, phosphorous, potassium, calcium, magnesium, sulfur, iron, manganese, copper, zinc, boron, molybdenum, or other derivatives to facilitate plant growth and/or balance soil pH.

The pyrolysis system may be mounted on two or more wheels and towed by the mobility platform. The pyrolysis system may also be physically mounted onto the robotic mobility system itself.

The robot includes a wireless communication system for bidirectional transmission of control and telemetry data to the cloud or to a human operator. The robot also includes a mesh wireless communication system for bidirectional transmission of control and telemetry data to other robots in the same area. The robot may communicate via established wireless standards including, wife, Bluetooth, sub gigahertz technology, LoRaWan, Satellite or cellular data connections.

Key abilities of the preferred robot include the ability to operate without supervision, the ability to be controlled by a remote operator, the ability to convert biomass into biochar, and the ability to thermally eliminate weeds. In some embodiments, the robot may be the size of a full size tractor. In some embodiments, the robot may be of small size, allowing operation in narrow rows and reducing or eliminating soil compaction because of its low weight.

The robot uses onboard sensors to identify and characterize the type, temperature, moisture content and composition of incoming biomass feedstock. Sensors are also used to identify the temperature and composition of exiting biochar. These sensors may include temperature sensors, thermal imaging systems, cameras, multispectral imaging systems or hyperspectral imaging systems. Such sensors shall also be used to identify open flames in proximity to the robot and automatically activate onboard fire suppression measures including dispersion of fire squelching agents including water, wetting agents, foam, dry chemicals, or dry powders.

In order to program the robot's path and navigation, a user first enters the GPS coordinates of the boundaries of the field of operation. This data can be entered via a PC, smartphone, tablet or a human machine interface (hmi) on the robot itself.

The user can then program a desired path of operation or allow the robot to determine the optimal path of operation. The operator can also control the robot directly via a remote control. A human operator can also manually input the desired temperature, oxygen concentration and residence time for the pyrolysis oven.

The robot navigates to its starting point and begins its process of navigation and path planning. Using its onboard sensors, the robot identifies features in its surroundings including but not limited to the shape and presence of rows. The robot may utilize its onboard cameras and a computer vision algorithm to identify the presence of rows. The robot also utilizes its onboard sensors to identify the presence of any obstacles that may impede its movement. The robot also uses its onboard sensors to identify any regions of high moisture content that might impede travel.

The robot uses a combination of its onboard sensors, GPS and navigational algorithms to determine an optimal path that covers the desired area while avoiding obstacles.

As the robot navigates its path, in addition to scanning for obstacles, it continuously monitors and characterizes the incoming biomass. Using sensors such as cameras, temperature sensors, thermal imaging systems, lidar and soil moisture sensors the robot captures and stores data about the incoming biomass. Using a combination of onboard algorithms, computer vision and data analysis techniques the robot determines the temperature, moisture content and chemical composition of the incoming biomass.

Using an internal algorithm, the robot continuously adjusts the temperature of the heat source, oxygen concentration of the pyrolysis system and the intensity of the blower or inert gas source to optimize pyrolysis. The robot also optimizes and adjusts the residence time of biomass in the pyrolysis chamber by changing its speed of travel. These pyrolysis process parameters can be adjusted to produce the desired amounts of biochar, pyrolysis gas and/or pyrolysis oil. These parameters can also be manipulated to produce a biochar with particular properties as determined by the user (full or incomplete carbonization). The robot can also adjust these process parameters to reduce emissions of gaseous material through the flue.

The robot uses a combination of onboard sensors including but not limited to cameras, temperature sensors, thermal imaging systems, and hyper/multi spectral imaging systems to monitor and characterize the biochar that is produced. The robot uses these sensors and an onboard computer vision algorithm to determine the temperature, composition, carbon content and moisture content of the biochar. Using data from these sensors, the robot then determines and applies an appropriate post processing treatment to the biochar.

Post-processing treatments may include cooling the biochar to a desired temperature, infusing it with nutrients or other soil amendments, or using a tilling or scouring attachment to incorporate the biochar into the soil. In order to cool the biochar, the robot may spray water, apply fire retardant or use a blower to reduce the temperature of the biochar. The robot may also use passive cooling system such as heat sinks, peltier coolers or refrigerators to reduce the temperature of the biochar.

The robot may inject or spray the biochar with soil amendment or other treatments such as fertilizer, compost, compost tea, nitrogen, pesticide, fungicide, herbicide and other additives to provide additional agricultural or soil amendment benefits.

The robot may also utilize a tilling attachment to aerate the soil and to incorporate the biochar into the soil.

The robot utilizes a combination of onboard sensors including cameras, lidar and ultrasonic sensors to measure the height of the incoming biomass. These data are processed by an internal algorithm. Based on the results of the algorithm, the robot can adjust the height of the pyrolysis system via actuators and lifts to accommodate the size of the incoming biomass.

As the robot navigates its environment, its onboard sensors capture environmental data (temperature, moisture, humidity) soil data (moisture, color, temperature, electrical conductivity) and images of the surrounding vegetation. These data can be stored internally and transmitted to the cloud for further analysis. These data can be used by the robot to infer and characterize plant health, plant size, plant growth and plant type of the surrounding vegetation. These data can also be used by the robot to infer the health and chemical composition of the soil, and the concentration of soil carbon. These data can be used to track the growth of plants over time. These data can also be used to track and monitor the carbon content of the soil.

If the robot encounters an obstacle, or detects that its movement is impeded using onboard GPS, positional and inertial sensors, the robot can attempt to navigate around the obstacle. If the robot is unable to navigate around the obstacle, it can safely shut down the pyrolysis system and alert a human operator.

When the robot reaches the end of a row, or a field boundary as determined by its GPS or user input, the robot will attempt to turn itself 180 degrees and proceed down the next row. In the event the robot cannot turn itself, it can safely shut down the pyrolysis system and alert a human operator.

The robot maintains an onboard fire detection system consisting of sensors including temperature sensors, thermal imaging systems, and cameras. If the robot detects fire or flame outside the pyrolysis system it can safely shut down the pyrolysis system and alert a human operator.

The robot includes an onboard fire suppression system consisting of a sprayer capable of spraying water or fire retardant around the robot. The robot can maintain an onboard tank of water or fire retardant, or connect to a remote tank via a hose. The robot may also with a dedicated fire suppression robot to coordinate automated fire control. If the fire suppression system is activated, the robot can safely shut off the pyrolysis system and alert a human operator.

The robot may include physical pretreatment attachments to treat and prepare the biomass feedstock for pyrolysis. These pretreatment attachments may include a spinning string or blade to cut or trim the biomass. These attachments may also include a mowing system to cut, mulch or reduce the size of the biomass before pyrolysis. In some embodiments, the pretreatment attachment may be a front mounted forage harvester or combine. The robot may also include a heat source to dry or preheat the biomass before pyrolysis.

While the primary purpose of the robot is to produce biochar, it may also be used to identify and thermally destroy weeds or other invasive plant species. Using its onboard sensors, cameras and computer vision algorithms, the robot can identify and characterize weeds or other invasive or undesired plants. The robot can then adjust the temperature of the heat source for the pyrolysis system to thermally destroy these plants. The system may include an actuator to physically position the heat source directly above the weed to minimize its impact on surrounding plants.

The robot can operate alone or in concert with other robots. When operated in concert with other robots, the user can set the desired path and boundaries via a fleet management platform. This fleet management platform can also be used to schedule and coordinate the activities of the robots.

The robot is powered by an onboard, rechargeable battery. This battery powers the mobility system, sensors, actuators and microcontrollers. The battery can also power the heat source. The battery can be charged electrically or through an onboard array of solar panels and solar charge controller. The battery can also be charged via an onboard gasoline, propane or diesel generator or a fuel cell. The robot can also carry an onboard fuel tank such as propane or natural gas to provide fuel for a burner as a heat source and power a generator. In some embodiments, the robot may be powered mechanically, either directly or partially from an internal combustion engine. The internal combustion engine may be a diesel engine, gasoline engine or mixed gas engine. In some embodiments, liquid natural gas, propane, kerosene, syngas, hydrogen gas, gasoline, diesel or combination thereof may be used as the fuel source.

The robot can be programmed to navigate and return to a particular geographic location when its battery charge is low. The robot can then connect to a charging station to recharge its internal battery. Once the internal battery is charged, the robot can resume its normal operations.

FIG. 1 shows an example of the pyrolysis system. A thermally-insulated metal housing 1 is mounted underneath the system to reduce the ingress of oxygen. A blower 2 is used to control the amount of oxygen present in the pyrolysis chamber. A flue 3 is installed to safely vent pyrolysis gases. A sensor array 4 is used to monitor the temperature and composition of the pyrolysis gas. A microcontroller 5 is used to control and optimize process parameters. A generator 6 is used to power the robot and heat source. A suite of sensors 7 is used to monitor and track pyrolysis parameters.

Figure 2:
FIG. 2 illustrates an example embodiment of the pyrolysis system in accordance with aspects of the present disclosure.

FIG. 2 shows the pyrolysis system 8 traveling along a field of dry biomass 9. The converted biochar 10 is shown exiting the pyrolysis chamber at high temperature as the system moves forward.

Figure 3:
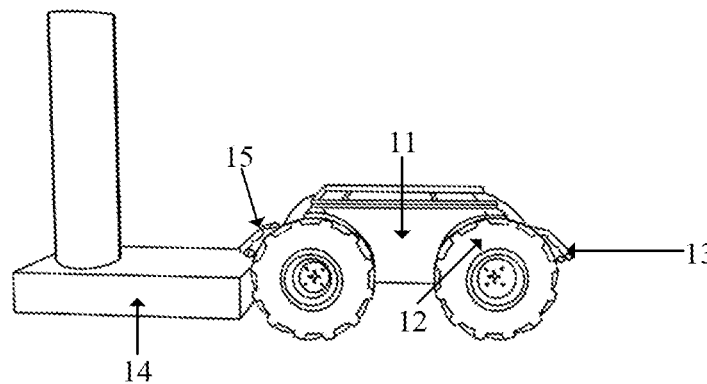
FIG. 3 illustrates an example embodiment of a robotic mobility system in accordance with aspects of the present disclosure.

FIG. 3 shows a robotic mobility system 11 with four drive wheels 12 and a suite of onboard sensors 13. The pyrolysis system 14 is towed behind the robotic mobility system and connected by a coupling 15.

Figure 4:
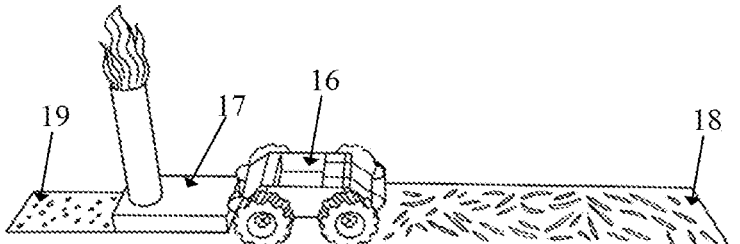
FIG. 4 illustrates an example embodiment of the robotic mobility system in accordance with aspects of the present disclosure.

FIG. 4 shows a robotic mobility system 16 pulling the pyrolysis system 17 across a row of biomass feedstock 18. The resultant biochar 19 is shown to exit the pyrolysis system as the robot moves forward.

Figure 5:
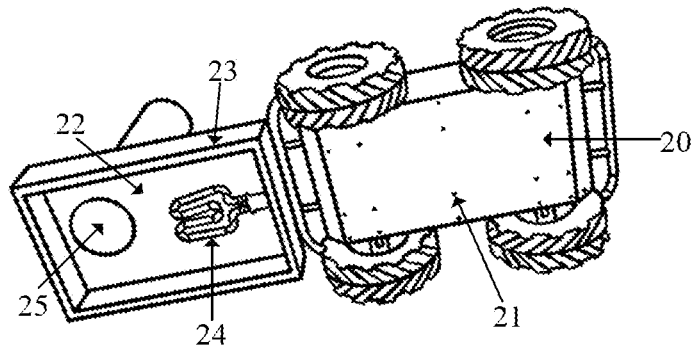
FIG. 5 illustrates an example embodiment of the robotic mobility system in accordance with aspects of the present disclosure.

FIG. 5 shows the underside of the robotic mobility system 20 with an array of sensors 21 towing the pyrolysis system 22 with insulated walls 23. The heat source 24 and flue 25 are visible.

Figure 6:
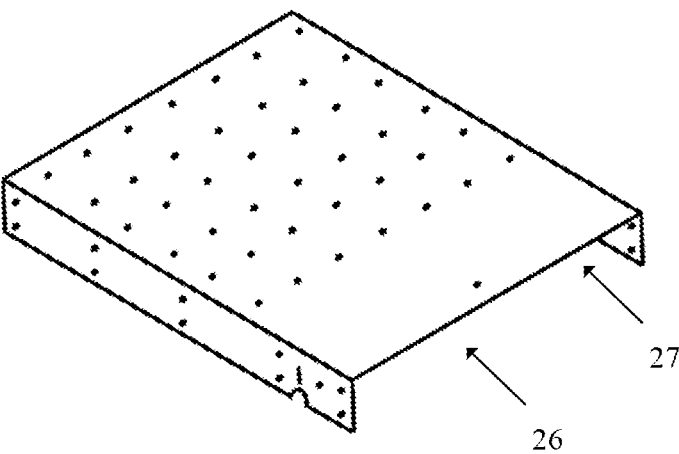
FIG. 6 illustrates an example embodiment of a metal housing for the pyrolysis system in accordance with aspects of the present disclosure.

FIG. 6 shows the insulated metal housing of the pyrolysis system 26 which may be open on one or more sides to allow biomass to enter and exit or partially sealed with a curtain 27 or series of metal louvers.

Figure 7:
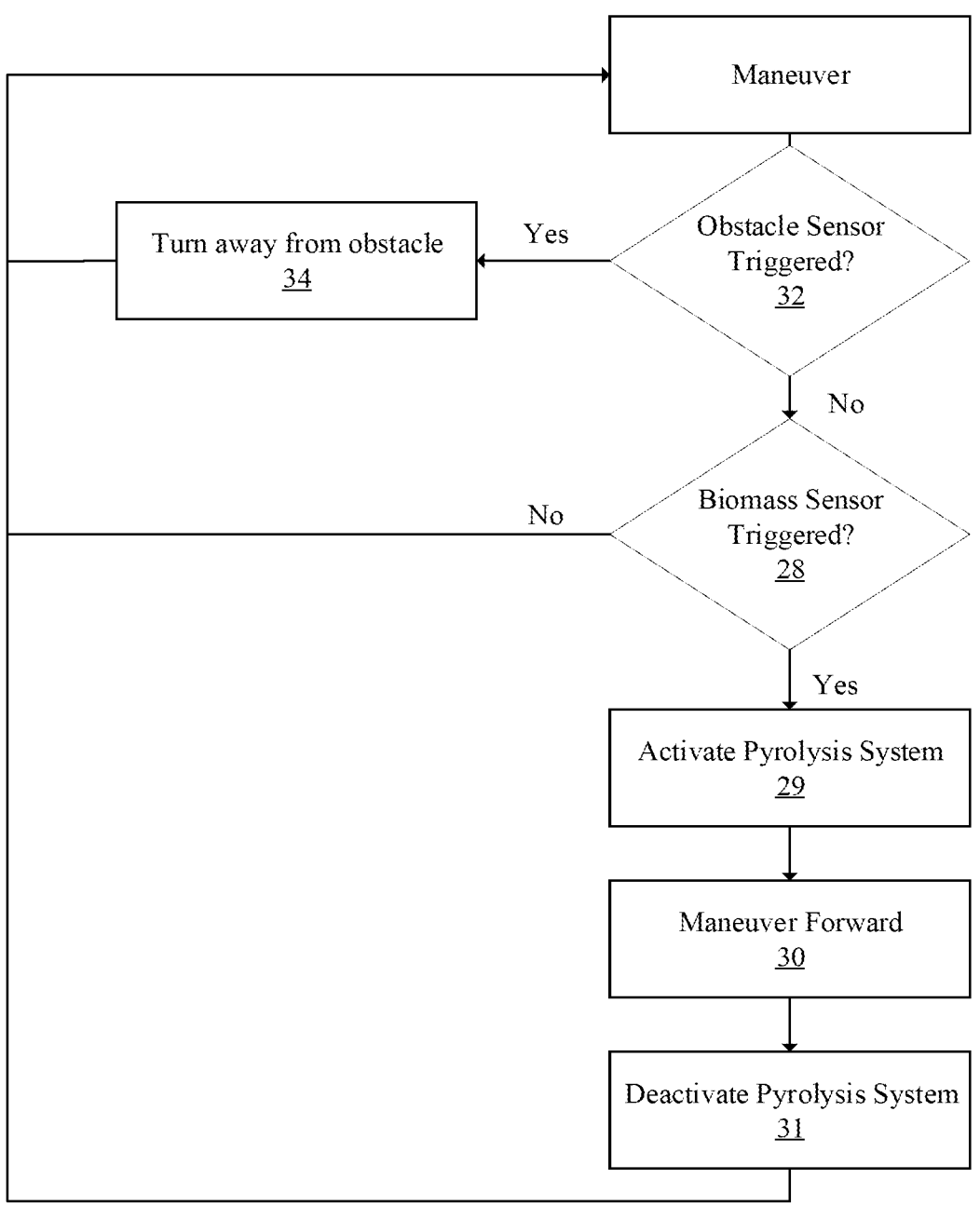
FIG. 7 illustrates an example flowchart of a process performed by the system in accordance with aspects of the present disclosure.

FIG. 7 is a flow chart depicting the primary steps associated with an exemplary method of the invention and also describing an example of the primary programming logic of the controller subsystem of a robot.

As shown in FIG. 7, when the controller subsystem receives a signal from the biomass sensor(s), step 28, the controller subsystem activates the biomass pyrolysis system, step 29, and may control the drive wheel motors to drive the robot forward, step 30, over the biomass, converting it to biochar. After a predetermined distance traveled and/or after a predetermined time of travel, the controller subsystem de-activates the pyrolysis system, step 31. In other embodiments, the robot is not maneuvered forward in order to convert the biomass to biochar. Then, the biomass pyrolysis system is not activated.

As shown in step 32-34, if the controller subsystem receives a signal from the obstacle sensor, the controller subsystem controls the drive wheel motors to turn and steer away from the crop/obstacle. The biomass pyrolysis system is not activated. In other designs, microcontrollers, application specific integrated circuitry, or the like are used. The controller subsystem preferably includes computer instructions stored in an on-board memory executed by a processor or processors. The computer instructions are designed and coded per the flow chart of FIG. 7 and the explanation herein.

Figure 8:
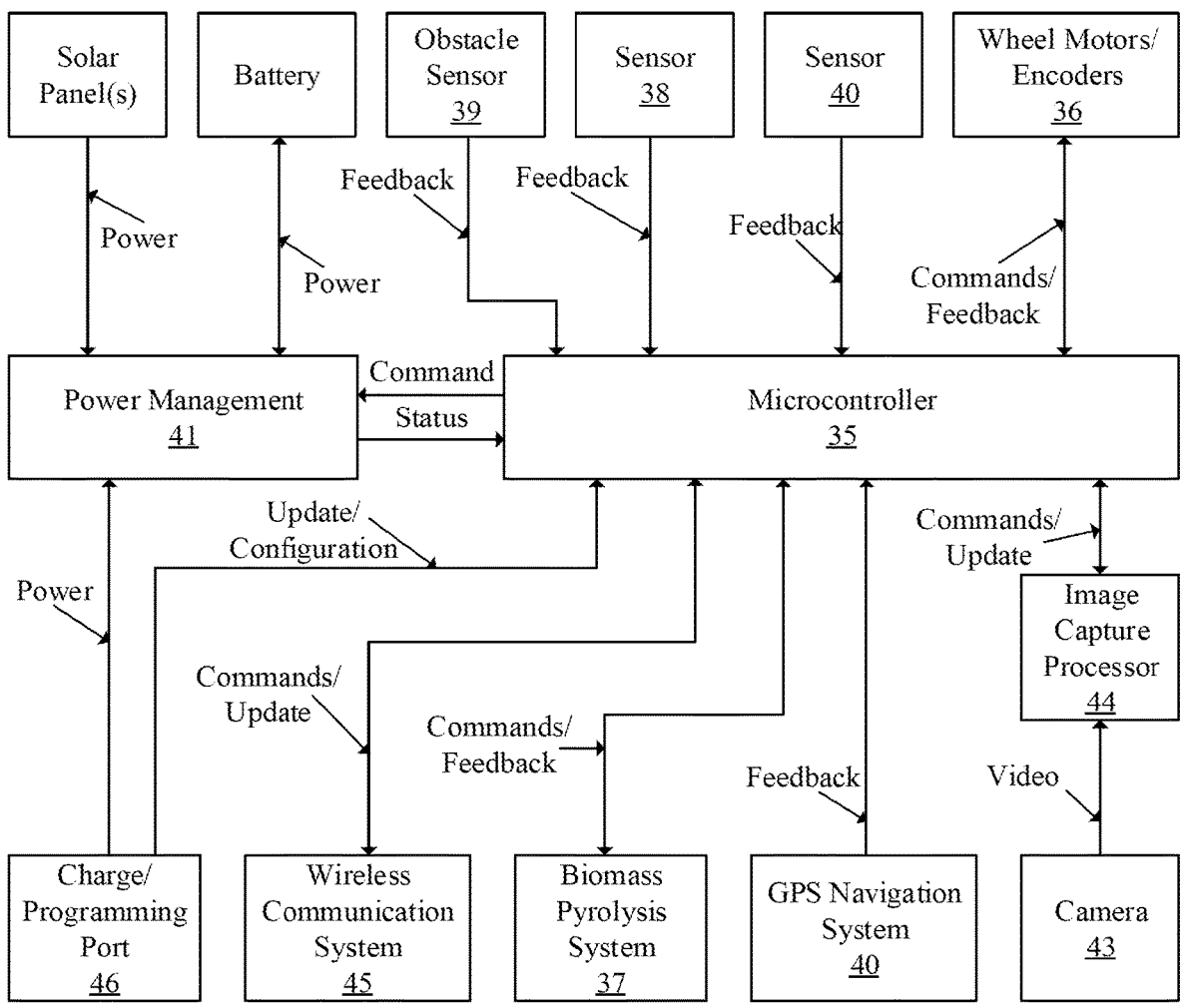
FIG. 8 illustrates an example embodiment of a controller subsystem in accordance with aspects of the present disclosure.

FIG. 8 shows controller subsystem 35 controlling drive motors 36 and biomass pyrolysis system 37 based on inputs from the biomass sensor(s) 38, the obstacle sensor(s) 39 and navigation system 40. FIG. 8 also shows power management controller 41. Further included may be one or more environmental sensors 42, an imager such as a camera 43, an image capture system 44, and a wireless communications subsystem (e.g., Bluetooth, cellular, or Wi-Fi), 45. FIG. 7 also shows charge and programming port 46.

Figure 9:
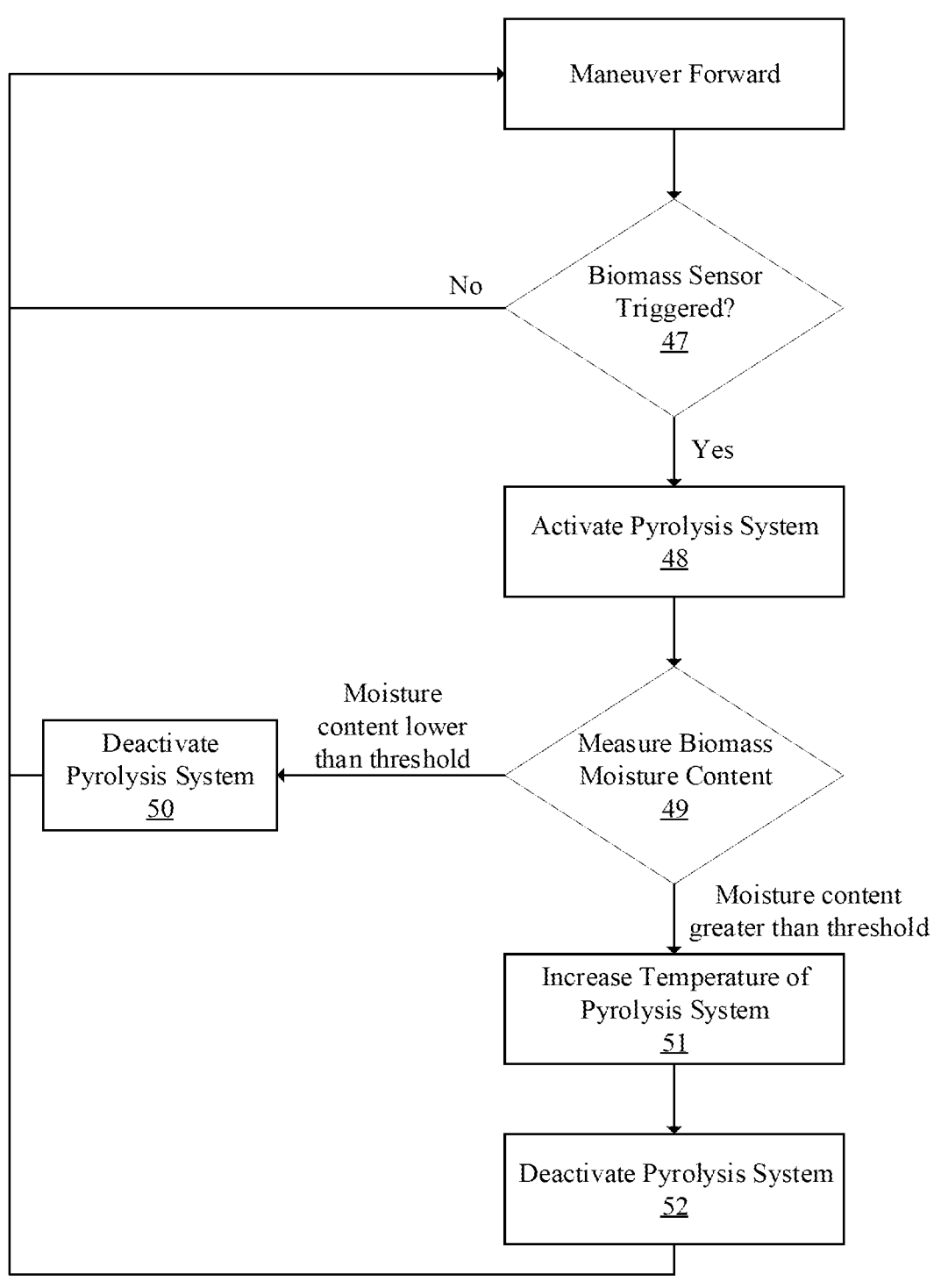
FIG. 9 illustrates an example flowchart of a process performed by the system in accordance with aspects of the present disclosure.

FIG. 9 shows a flow chart depicting the primary steps associated with an exemplary method of the invention and also describing an example of the primary programming logic of the controller subsystem of a robot.

As shown in FIG. 9, when the controller subsystem receives a signal from the biomass sensor(s), step 47, the controller subsystem activates the biomass pyrolysis system, step 48, and then measures the moisture content of the incoming biomass using a suite of sensors, step 49. If the moisture content of the biomass is at or below a set threshold, the pyrolysis system is deactivated, step 50, and the robot maneuvers forward. If the moisture content of the biomass feedstock is detected to be below a set threshold, the temperature of the pyrolysis system is increased, step 51, and subsequently deactivated, step 52. The robot then maneuvers forward.

Figure 10:
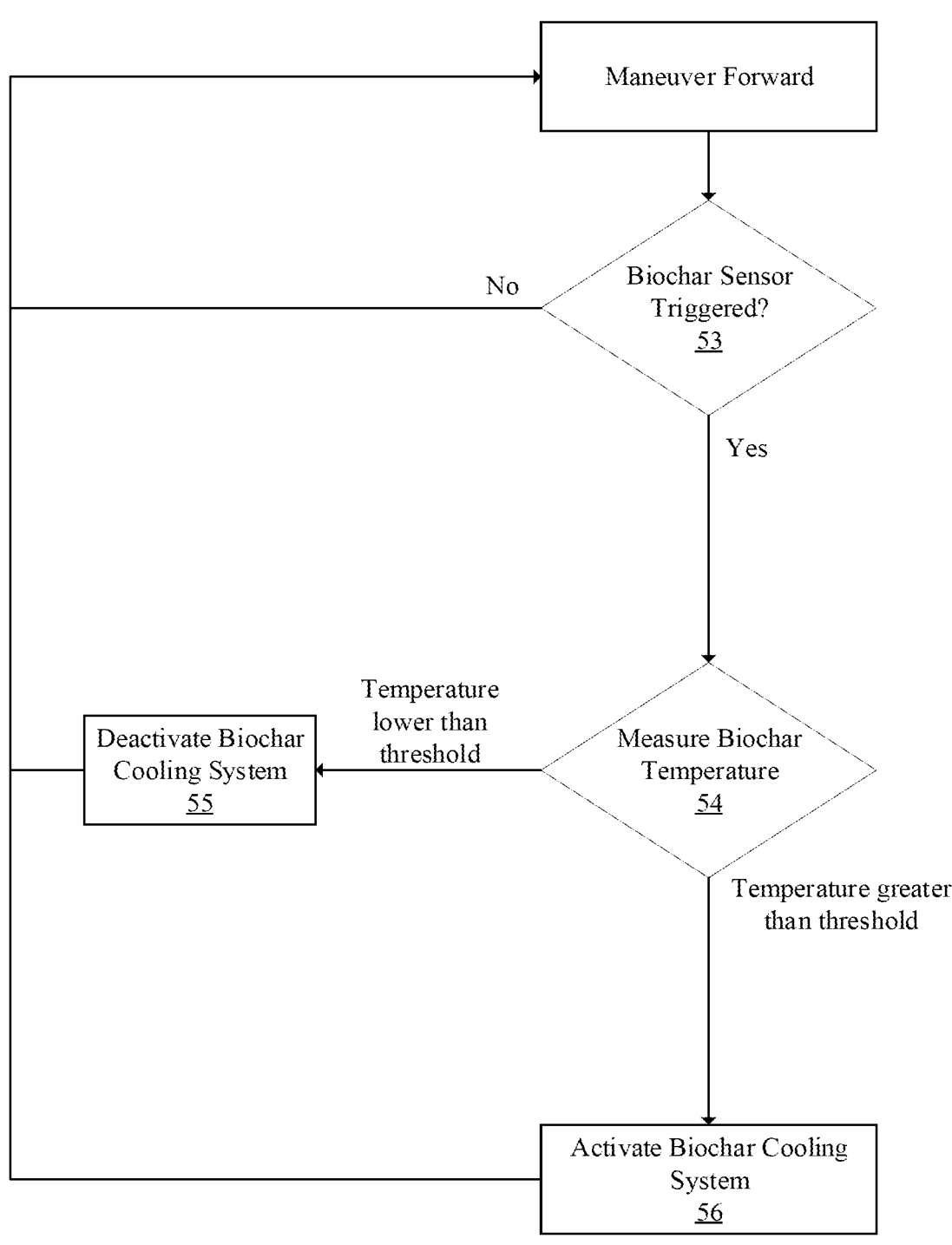
FIG. 10 illustrates an example flowchart of a process performed by the system in accordance with aspects of the present disclosure.

As shown in FIG. 10, when the controller subsystem receives a signal from the biochar sensor(s), step 53, the controller subsystem activates the biochar temperature sensor and then measures the temperature of the exiting biochar using a suite of sensors, step 54. If the temperature of the biochar is at or below a set threshold, the biochar cooling system is deactivated, step 55, and the robot maneuvers forward. If the temperature of the biochar is detected to be above a set threshold, the biochar cooling system is activated, step 56, and the robot then maneuvers forward.

Figure 11:
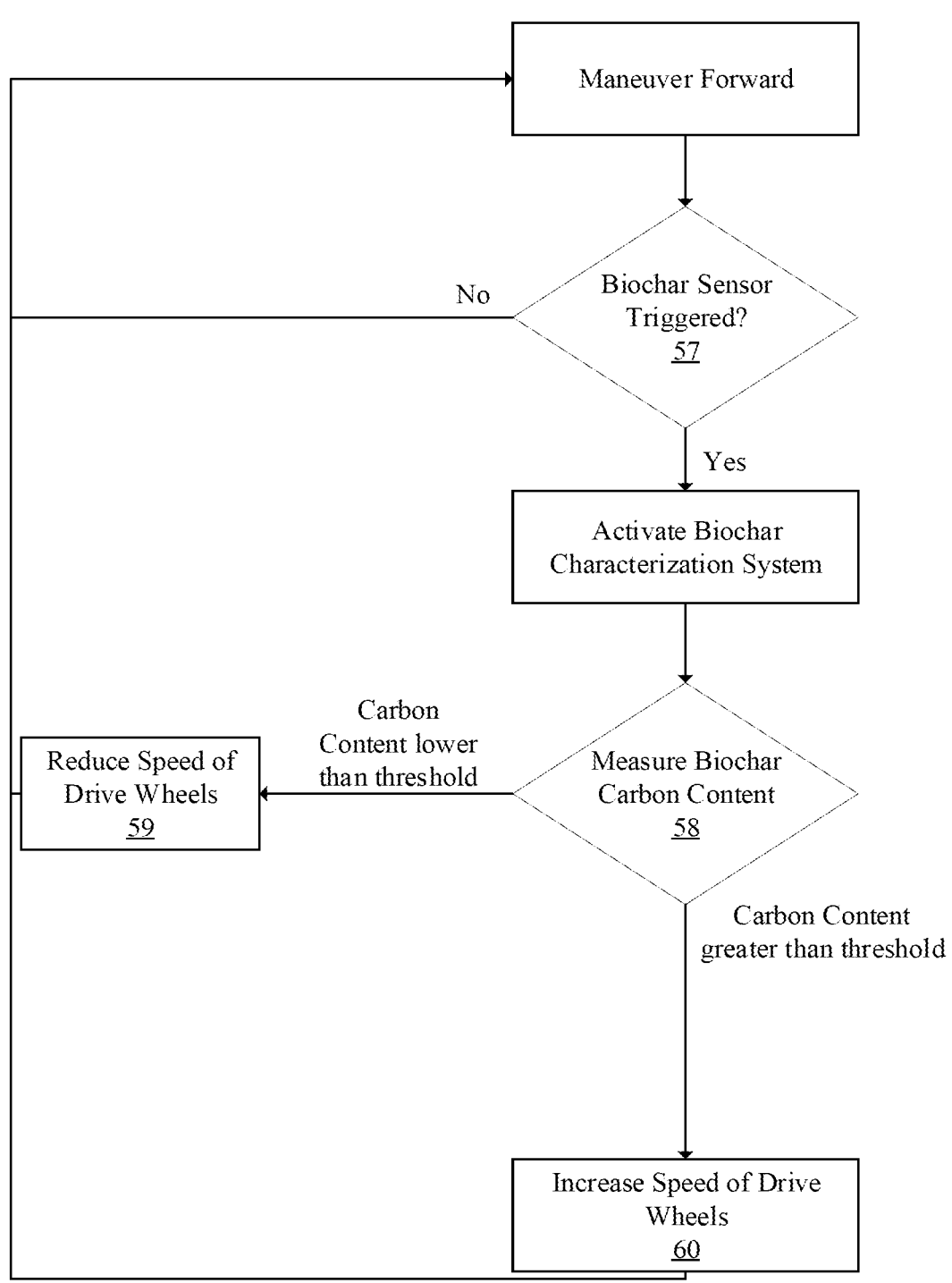
FIG. 11 illustrates an example flowchart of a process performed by the system in accordance with aspects of the present disclosure.

As shown in FIG. 11, when the controller subsystem receives a signal from the biochar sensor(s), step 57, the controller subsystem activates the biochar characterization system and then measures the carbon content of the exiting biochar using a suite of sensors, step 58. If the carbon content of the biochar is at or below a set threshold, the speed of the drive wheels is decreased, step 59, and the robot maneuvers forward. If the carbon content of the biochar is detected to be above a set threshold, the speed of the drive wheels is increased, step 60, and the robot then maneuvers forward.

Figure 12:
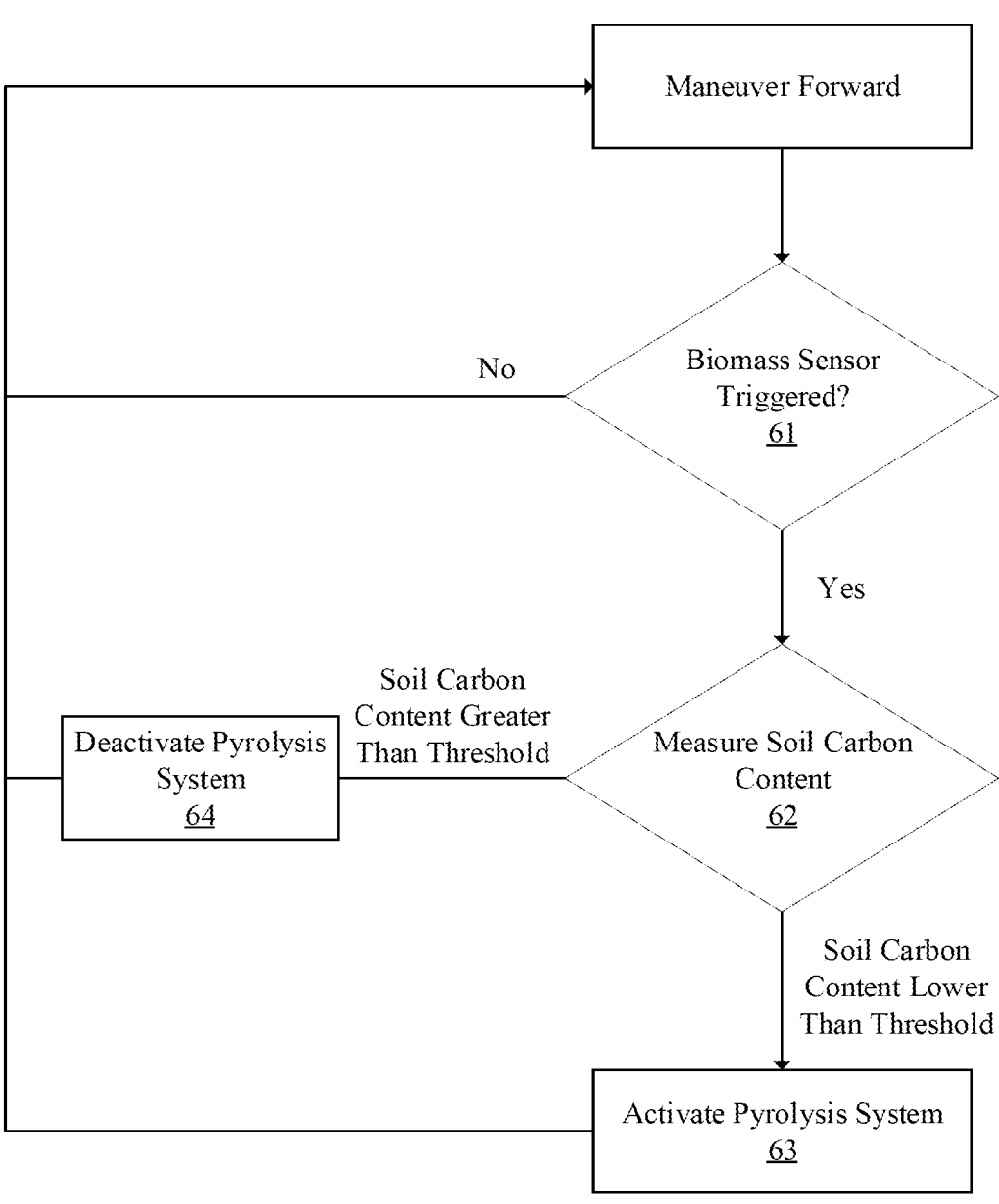
FIG. 12 illustrates an example flowchart of a process performed by the system in accordance with aspects of the present disclosure.

As shown in FIG. 12, when the controller subsystem receives a signal from the biomass sensor(s), step 61, the controller subsystem activates the soil characterization system and then measures the carbon content and other chemical and physical properties of the soil using a suite of sensors, step 62. If the carbon content of the soil is at or below a set threshold, the pyrolysis system is activated, step

63, and the robot maneuvers forward. If the carbon content of the soil is detected to be above a set threshold, the pyrolysis system is deactivated, step 64, and the robot then maneuvers forward.

Figure 13:
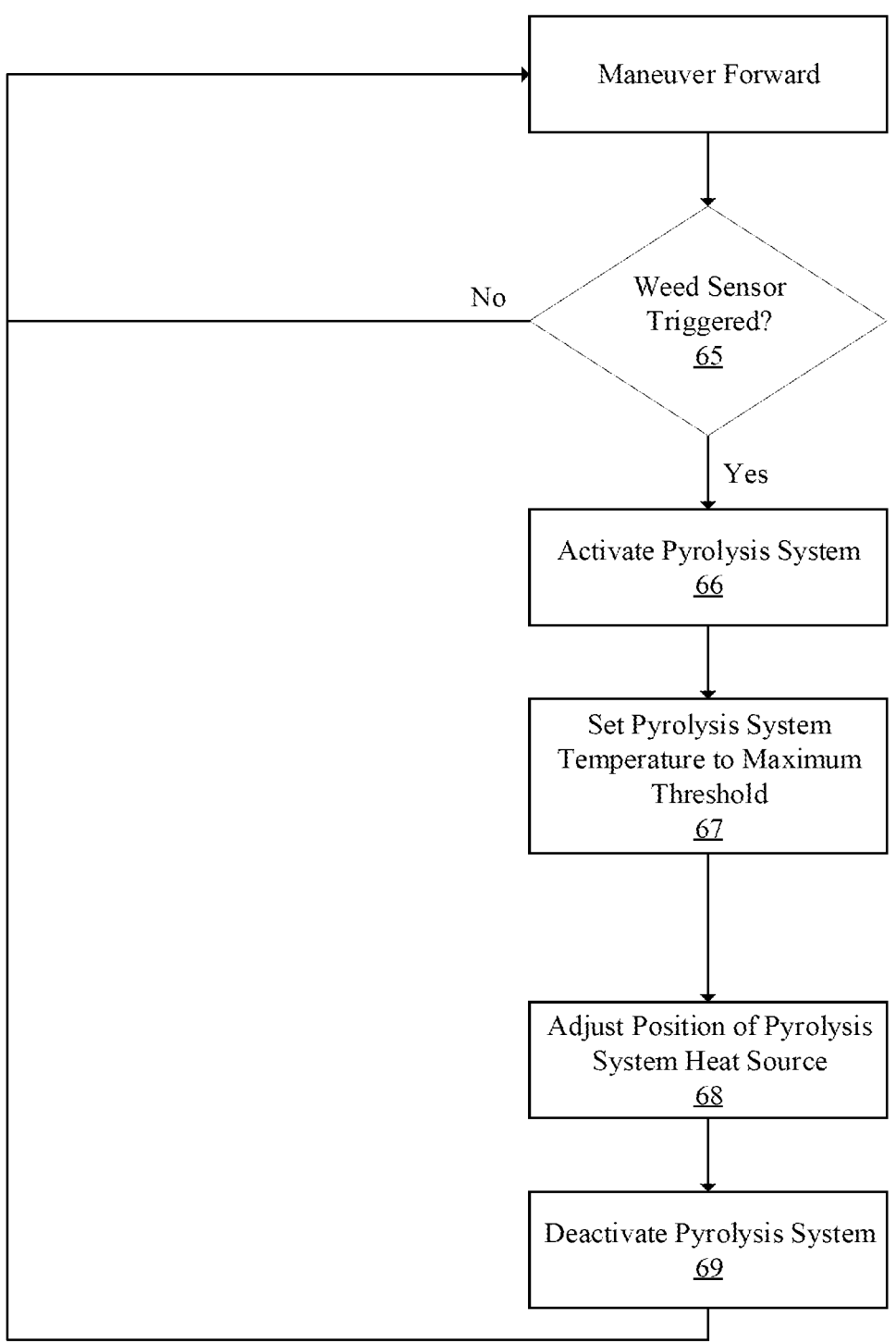
FIG. 13 illustrates an example flowchart of a process performed by the system in accordance with aspects of the present disclosure.

As shown in FIG. 13, when the controller subsystem receives a signal from the weed sensor(s) indicating the presence and location of a weed or other invasive plant species, step 65, the controller subsystem activates the pyrolysis system, step 66, and then sets the pyrolysis system temperature to a maximum threshold, step 67. The robot then uses an actuator to adjust the position of the pyrolysis system heat source to be in close physical proximity to the weed, step 68, to thermally destroy the weed. The robot then deactivates the pyrolysis system, step 69, and moves forward.

Figure 14:
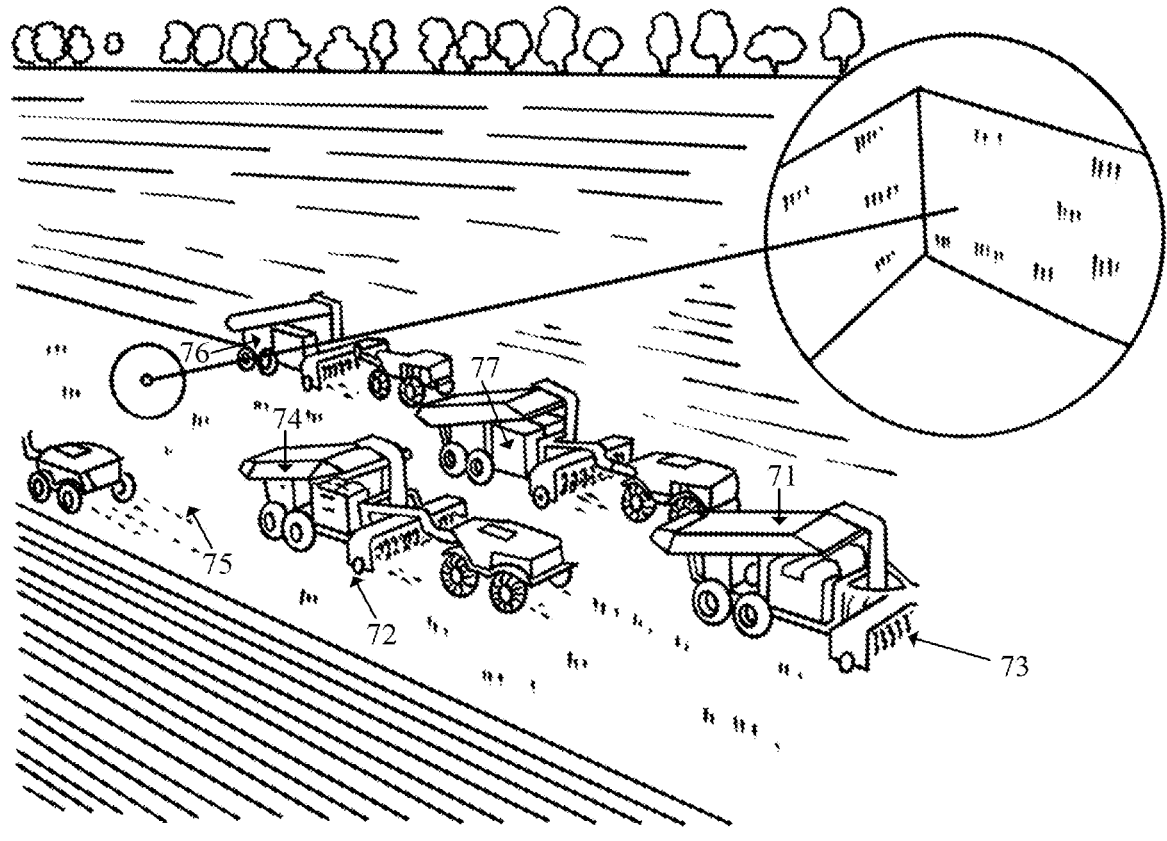
FIG. 14 illustrates an example of a fleet of robots operating in a synchronized fashion in accordance with aspects of the present disclosure.

As shown in FIG. 14, a fleet of automated pyrolysis robots, step 71, are dispatched to a plot of land. The robots position, heading and speed is monitored, synchronized and controlled by a centralized fleet management platform, step 72. The robots collect and process raw biomass, step 73, and thermally convert it to biochar, step 74. The resultant biochar is then dispensed onto the soil surface, step 75, or tilled into the topsoil using an onboard tiller, step 76, or collected and bagged using an on-board bagging system, step 77.

Figure 15:
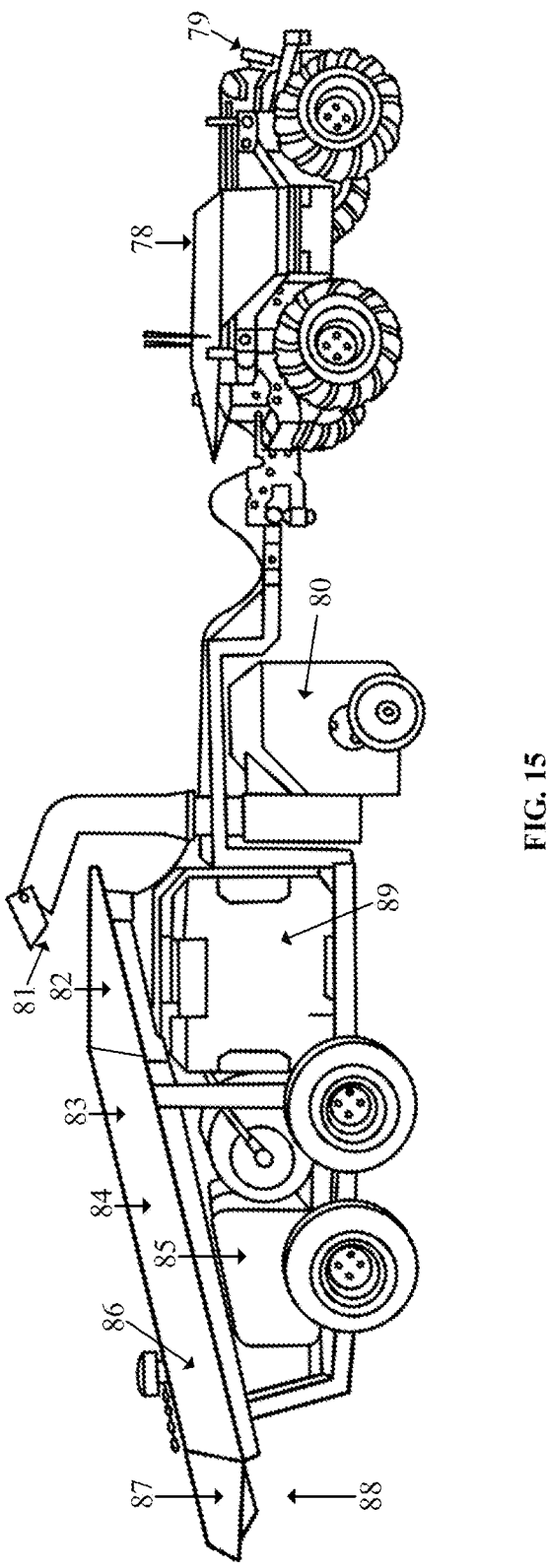
FIG. 15 illustrates an example embodiment of the complete system with an autonomous lead vehicle in accordance with aspects of the present disclosure.

As shown in FIG. 15, the system is driven by a lead vehicle, step 78, which may consist of an autonomous robotics platform, a tractor, an all-terrain vehicle or a light electric vehicle. Sensors, lidar and cameras on board the lead vehicle capture information about the environment, and biomass ahead of the vehicle, step 79. Data collected may include the biomass moisture content, size, mass, color and type. Biomass is collected and processed to a predetermined size and bulk density using a modular biomass processing system, step 80, based on data collected by sensors on the lead vehicle. Biomass is then conveyed to a hopper for temporary storage and, if necessary, further drying, step 81. Based on data collected from onboard sensors, the biomass in the hopper is dried and further processed to a predetermined moisture level, step 82. Once dried, biomass is loaded into the biochar processing system, step 83. The temperature and residence time of the biochar processing system is determined by the system's onboard computer and data collected from sensors, step 84. The resultant biochar is cooled to a predetermined temperature using a combination of heat sinks, fans and irrigation with water from an onboard or remote reservoir, step 85. Additives including but not limited to chemical or organic fertilizer may then be added to the biochar from an onboard or remote reservoir, step 86. The resultant biochar, including any additives, is then measured using an array of onboard sensors and cameras, step 87. Measurements may include mass, temperature, carbon content, cation exchange capacity, nitrogen content, phosphorous content, pH, color, texture, density and particle size. The biochar is then tagged with a GPS coordinate and dispensed onto the soil surface, or tilled into the topsoil, or bagged for future use, step 88. The system is powered via onboard batteries, which are charged using an onboard generator powered by a combustible fuel or onboard or remote solar panels, step 89.

Figure 16:
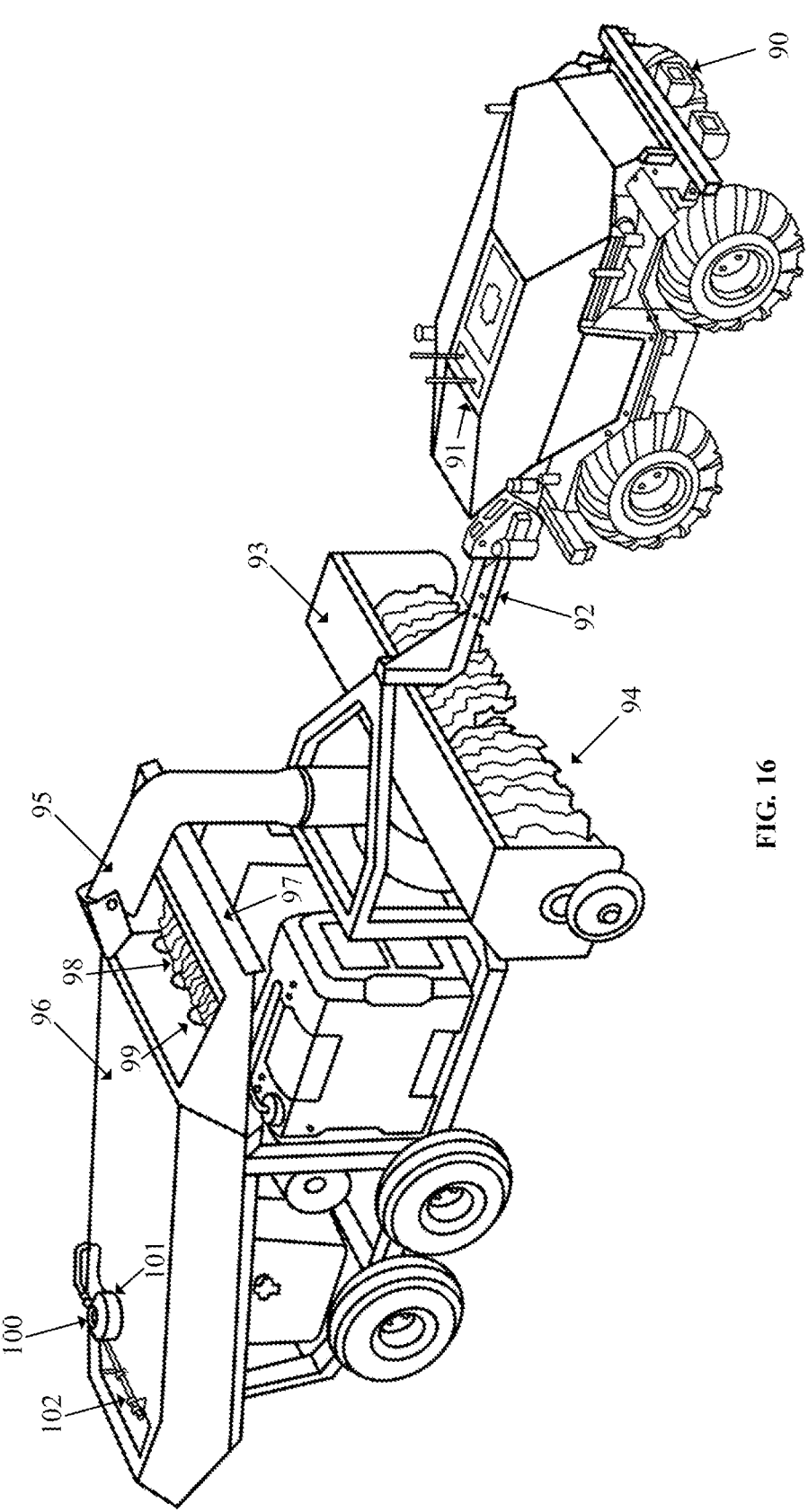
FIG. 16 illustrates an example embodiment of the complete system with an autonomous lead vehicle in accordance with aspects of the present disclosure.

As shown in FIG. 16, the robot and lead vehicle include a number of onboard sensors such as RGB cameras, depth cameras, LiDAR, inertial measurement units, GPS, temperature, humidity, environmental sensors, radar and ultrasound, step 90. The robot and lead vehicle also have an array of wireless communication equipment including cellular, wifi and satellite connectivity, step 91. The lead vehicle is attached to the robot via a tow hitch, step 92. Biomass is collected and processed using a modular biomass processing system, step 93. The modular biomass processing system 93 may be mounted behind the robot, between the robot and the biochar production system 96, as shown. The modular biomass processing system 93 may also be mounted at the front of the robot. The biomass processing unit 93 may also be mounted at the front or back of a manually driven tractor. All components may be connected to a tractor in the same manner as they are connected to the robot. The processing system may consist of an array of cutting tools whose pitch, speed and position can be adjusted depending on the type, size, density and moisture content of the incoming biomass, step 94. The biomass is processed to a predetermined size and consistency, and then conveyed using air or a mechanical mechanism to the loading hopper, step 95. The biomass is further dried and preheated to a predetermined moisture concentration and temperature using a combination of onboard heating elements and hot exhaust gas from the biochar production system, step 96. The mass, color, particle size and type of biomass is recorded using an array of onboard sensors, step 97. An array of mechanical implements attached to augers in the hopper are used to further process the biomass and load it into the biochar production system, step 98. The robot may include a single or multiple biochar production systems and augers operating in parallel, step 99. In some embodiments, multiple pyrolyzing augers may be operated in parallel to increase capacity and throughput. Exhaust gases from the biochar production system are vented and/or flared using an exhaust vent, step 100. An Array of onboard sensors measure and track the composition of the exhaust gas, step 101. An onboard sprayer applies water and additives including chemical or organic fertilizer to the produced biochar to reduce the temperature and apply nutrients or other soil amendments, step 102.

Figure 17:
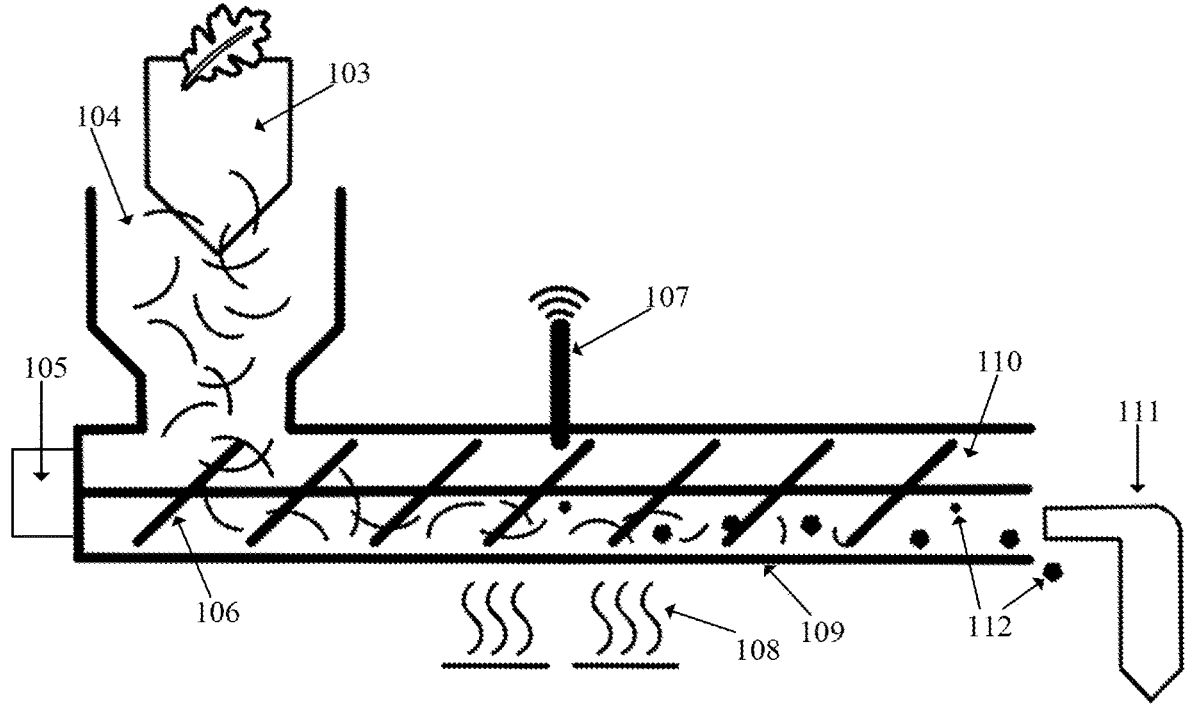
FIG. 17 illustrates an example of the biochar production system and pyrolysis reactor in accordance with aspects of the present disclosure.

As shown in FIG. 17, biomass is loaded into a hopper, step 103, where it is weighed and characterized according to moisture content, color and type. A combination of heating elements and exhaust gases from the biochar reactor are used to further dry and preheat the biomass, step 104. Biomass is loaded into the biochar reactor using an electrically-driven or mechanically-driven auger, whose speed can be controlled by the system's onboard computer, step 105. Biomass is driven through the reactor by the rotating auger, step 106. An array of sensors are embedded into the walls of the reactor including temperature, cameras, moisture, humidity and gas concentration sensors, step 107. The chamber and/or auger are heated using a resistance or induction heating source, and/or flame heat from burning fuel and exhaust gas, and/or a light source such as a laser emitter, step 108. The temperature of the reactor is controlled across its length by the system's onboard computer, which adjusts the temperature of the heating sources, step 109. The reactor may be operated at atmospheric pressure, or may be purged of oxygen by injecting an inert gas such as nitrogen or carbon dioxide, step 110. The heated biochar is ejected from the system using the auger, step 111. A conductive material such as metal beads or shot may be mixed with the incoming biomass and mechanically or magnetically removed from the biochar to improve heat transfer within the auger, step 112.

Figure 18:
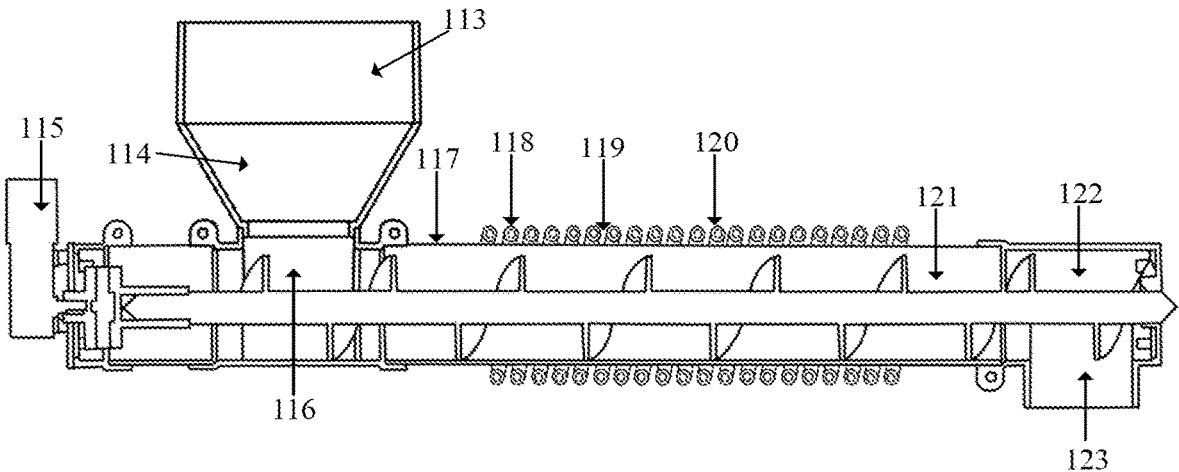
FIG. 18 illustrates an example of the biochar production system and pyrolysis reactor in accordance with aspects of the present disclosure.

As shown in FIG. 18, biomass is loaded into a hopper, step 113, where it is weighed and characterized according to moisture content, color and type. A combination of heating elements and exhaust gases from the biochar reactor are used to further dry and preheat the biomass, step 114. Biomass is loaded into the biochar reactor using an electrically-driven or mechanically-driven auger, whose speed can be controlled by the system's onboard computer, step 115. Biomass is driven through the reactor by the rotating auger, step 116. An array of sensors are embedded into the walls of the reactor including temperature, cameras, moisture, humidity and gas concentration sensors, step 117. The chamber and/or auger are heated using a resistance or induction heating source, and/or flame heat from burning fuel and exhaust gas, and/or a light source such as a laser emitter, step 118. In the case of induction, the induction coils are wrapped around the length of the reactor, which may be covered in insulating material such as refractory or mineral wool, step 119. The temperature of the reactor is controlled across its length by the system's onboard computer, which adjusts the temperature of the heating sources, step 120. The reactor may be operated at atmospheric pressure, or may be purged of oxygen by injecting an inert gas such as nitrogen or carbon dioxide, step 121. The heated biochar is ejected from the system using the auger, step 122. A conductive material such as metal beads or shot may be mixed with the incoming biomass and mechanically or magnetically removed from the biochar to improve heat transfer within the auger, step 123.

Figure 19:
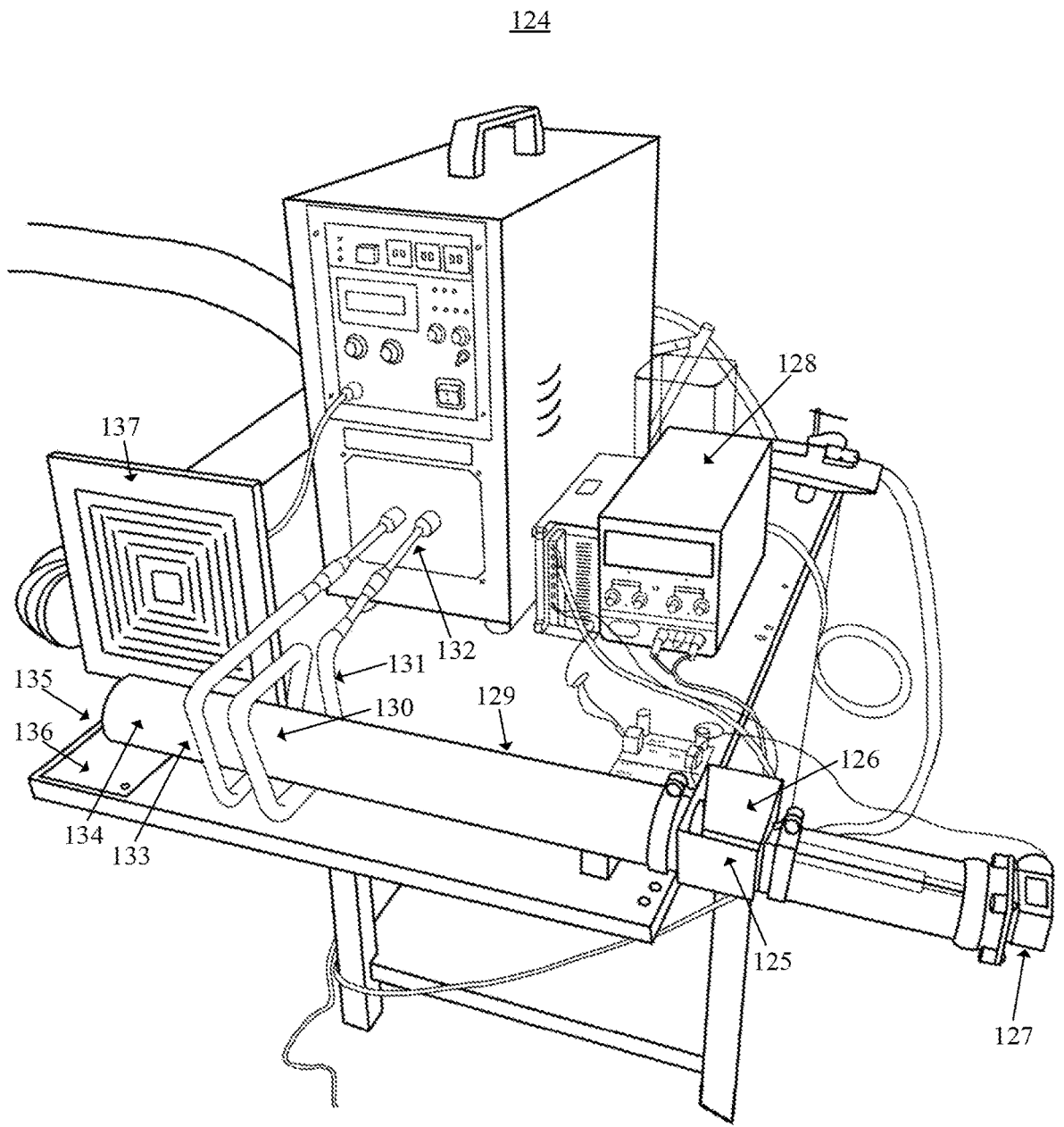
FIG. 19 illustrates an example of a stationary biochar production system and pyrolysis reactor heated by induction heating elements in accordance with aspects of the present disclosure.

As shown in FIG. 19, the biochar production system can operate as a standalone, stationary and/or mobile system, step 124. Biomass is loaded into a hopper, step 125, where it is weighed and characterized according to moisture content, color and type. A combination of heating elements and exhaust gases from the biochar reactor are used to further dry and preheat the biomass, step 126. Biomass is loaded into the biochar reactor using an electrically-driven or mechanically-driven auger, whose speed can be controlled by the system's onboard computer, step 127. Biomass is driven through the reactor by the rotating auger powered by an electric power supply, or mechanical drive, step 128, at a rate determined by the system's onboard computer and data from sensors. An array of sensors are embedded into the walls of the reactor including temperature, cameras, moisture, humidity and gas concentration sensors, step 129. The chamber and/or auger are heated using a resistance or induction heating source, and/or flame heat from burning fuel and exhaust gas, and/or a light source such as a laser emitter, step 130. In the case of induction, the induction coils are wrapped around the length of the reactor, which may be covered in insulating material such as refractory or mineral wool, step 131. In the case of induction, an induction furnace and power supply are used to charge the induction coil and circulate cooling water, step 132. The temperature of the reactor is controlled across its length by the system's onboard computer, which adjusts the temperature and power of the heating sources, step 133. The reactor may be operated at atmospheric pressure, or may be purged of oxygen by injecting an inert gas such as nitrogen or carbon dioxide, step 134. The heated biochar is ejected from the system using the auger, step 135. A conductive material such as metal beads or shot may be mixed with the incoming biomass and mechanically or magnetically removed from the biochar to improve heat transfer within the auger, step 136. An exhaust system generates negative air pressure to capture and safely vent or flare any emissions or exhaust gases generated by the system, step 137.

Figure 20:
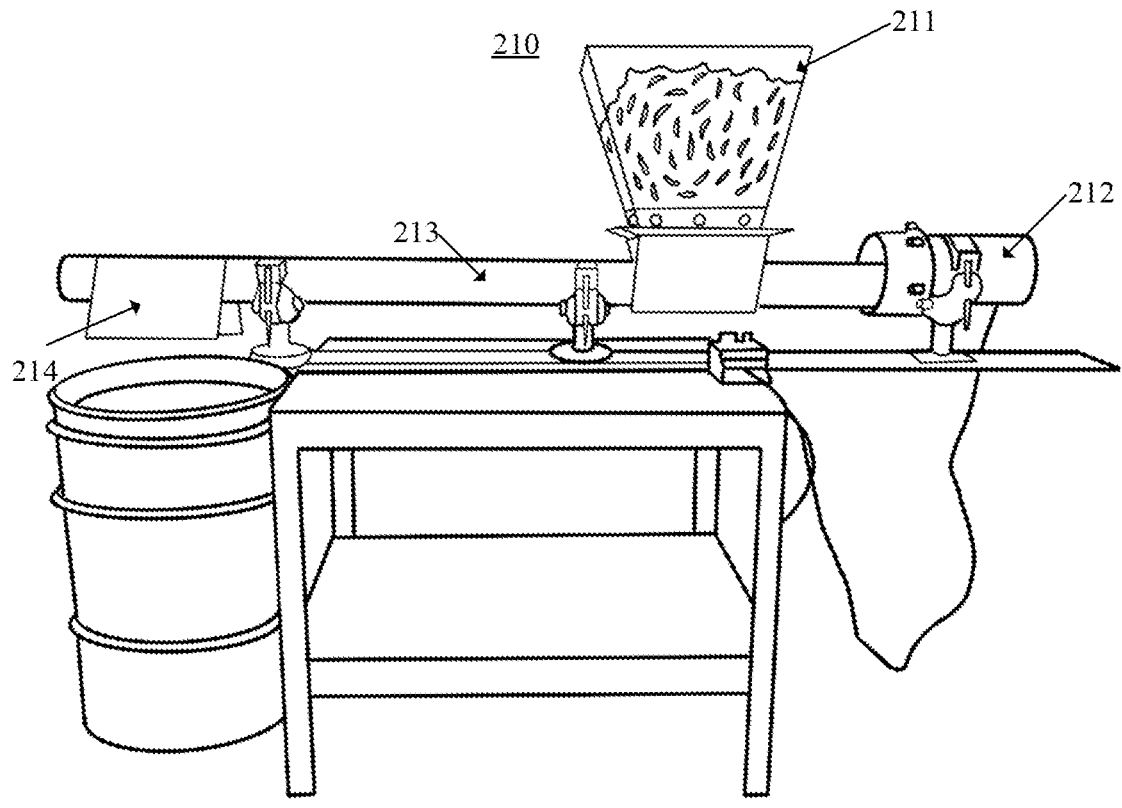
FIG. 20 illustrates an example of a stationary biochar production system and pyrolysis reactor heated by induction heating elements in accordance with aspects of the present disclosure.

FIG. 20 is an example of a stationary biochar production system 210 and pyrolysis reactor 213 heated by induction heating elements, similar to that of FIG. 19. The stationary biochar production system may comprise a hopper 211 to hold biomass feedstock to be fed into the pyrolysis reactor. An auger driving motor 212 may be used to turn a pyrolytic auger. The pyrolytic auger may transport biomass feedstock from the hopper 211 into the pyrolysis reactor 213 to pyrolyze and/or combust the biomass feedstock. The biochar generated in the pyrolysis reactor 213 may be further carried by the pyrolytic auger or a quenching auger to a biochar handling system 214. The biochar handling system 214 may be configured to feed the biochar into a storage container or onto a conveyance system to store or apply the biochar at a different location.

Figure 21A:
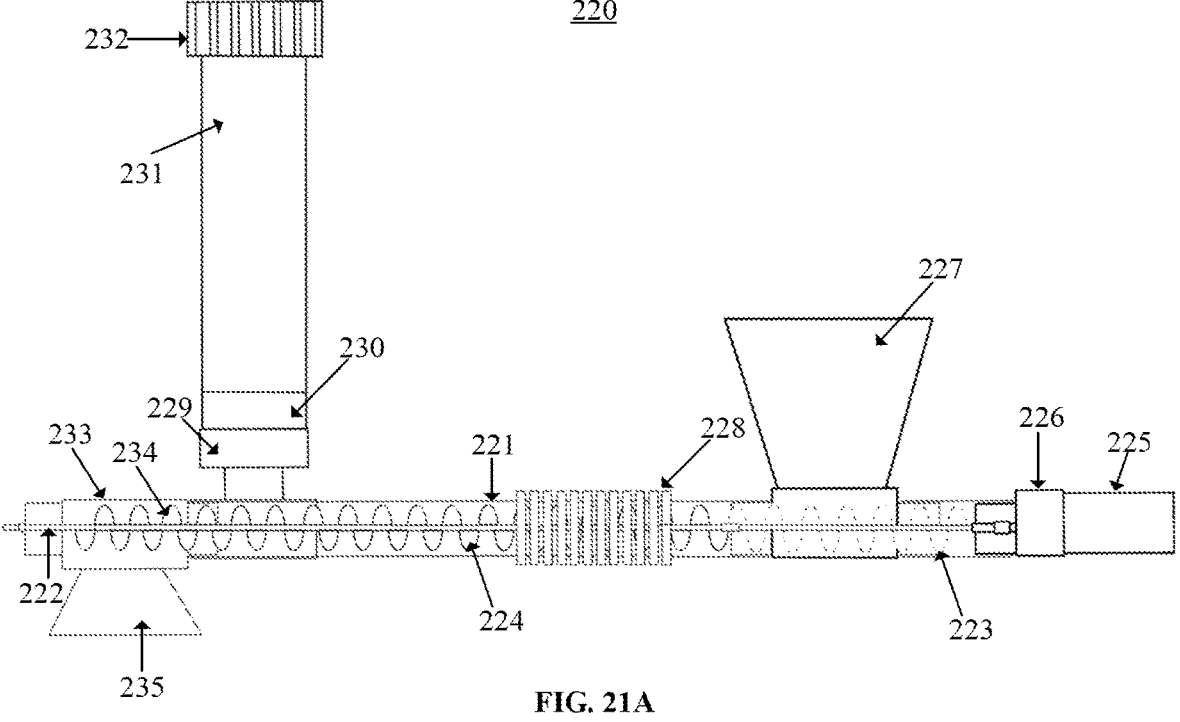
FIG. 21A illustrates an example of the biochar production system and pyrolysis reactor in accordance with aspects of the present disclosure.

FIG. 21A illustrates an example of the biochar production system and pyrolysis system 220 in accordance with aspects of the present disclosure. The pyrolysis system 220 may comprise one or more thermally insulated enclosures 221, one or more auger drive motors 225, one or more gear reducers 226, a hopper 227, an exhaust system, one or more cooling and quenching systems 233 and one or more biochar handling systems 235.

The thermally insulated enclosure 221 may comprise one or more auger shafts 222, one or more cut flights 223, one or more standard flights 224 and induction heating zone 228.

The cut flights 223 and/or the standard flights 224 may be of fixed or variable pitch. The cut flights 223 may be comprise one or more cuts to the flight and/or comprise cut and folded flights. The cut flights 223 may further process biomass by cutting the biomass while pushing the biomass into the thermally insulated enclosure. Once in the thermally insulated enclosure, standard flights carry the biomass into the induction heating zone 228 for pyrolyzation. Induction coils may be wrapped around the induction heating zone to create a pyrolytic reactor section of the thermally insulated enclosure. The induction heating zone 228 may induce heating of the thermally insulated enclosure, the auger shaft 222, the auger standard flights 224 and any metallic conductive material added to the biomass to induce additional heat from within the biomass itself. The addition of conductive material, such as metallic shot, may provide an even heating of the biomass material. Additional or alternative heating sources may be used to drive the pyrolyzation of biomass in the pyrolytic reactor section. Within the pyrolytic reactor section, both pyrolysis reaction may occur simultaneously with combustion reactions. The balance between the pyrolytic reactions and the combustion reactions may be controlled by adjusting the parameters inside the pyrolytic reactor. Injection of exhaust gas, inert gas, atmospheric gas or steam may be used to control the amount of pyrolysis and combustion occurring at any time in the pyrolytic reactor. The injection of atmospheric gas into the chamber may increase the amount of combustion occurring in the pyrolytic reactor. Injection of exhaust gas or inert gas may decrease or eliminate combustion in the reactor. Injection of steam may be used to drive a gasification reaction in the reactor to generate syngas or other desirable and/or combustible byproducts.

The flight configuration may determine material flow and ability to mitigate feedstock bridging. The auger flights 223 and 224 may be interchangeable with flights better suited for the biomass being processed.

The auger drive motor 225 may be coupled to the one or more auger shafts 222 by one or more gear reducers 226. The rate of turning of the auger shaft 222 may be varied based on speed of travel of the tractor pulling the pyrolysis system 220, the desired residence time, or characteristics of the biomass feedstock being collected and fed into the hopper 227. Biomass with a higher moisture content may require a slower turning rate to compensate for the added moisture in the pyrolysis reactor.

The exhaust system may comprise enclosure/exhaust coupler 229, a catalytic combustor 230, a chimney stack 231 and an up-draft assist 232. The exhaust gases produced by the pyrolyzation of biomass in the pyrolytic reactor may be directed through an enclosure/exhaust coupler 229 and into a catalytic combustor 230. The catalytic combustor 230 may be used to lower the combustion temperature of the smoke and vapor in the exhaust gases, allowing for a complete combustion of non-pyrolyzed material that are given off as exhaust. The chimney stack 231 and up-draft assist 232 may provide channel the exhaust gas out of the pyrolytic reactor for further processing or venting into the atmosphere. Combusted and/or uncombusted exhaust gasses may be redirected from the chimney stack 231 back into the pyrolytic reactor. The up-draft assist 232 may include a flare component to burn any remaining unburned smoke before it leaves the system.

Cooling and quenching system 233 may comprise a cooling auger 234, active and passive cooling components, a nutrient integrator and one or more biochar sensor arrays. Active cooling may be accomplished by spraying water, applying fire retardant or using a blower to reduce the temperature of the biochar. Passive cooling may be accomplished by using heat sinks, peltier coolers or refrigeration units to reduce the temperature of the biochar.

The sensor arrays in the cooling and quenching system 233 may be used to determine, characterize and monitor the composition of the biochar. Based on the determined composition, the nutrient integrator may infuse nutrients and/or soil amendments directly into the biochar. The biochar may be infused with fertilizer, compost, compost tea, nitrogen, pesticide, fungicide, herbicide, bacteria, yeast, fungi and other additives. In some embodiments, the biochar may also be mixed with non-pyrolyzed crop residue before being applied to the soil or stored. The nutrient integrator may also integrate fluids with the biochar for cooling. Fluids may comprise Nitrogen, Phosphorous, Potassium, Calcium, Magnesium, Sulfur, Iron, Manganese, Copper, Zinc, Boron, Molybdenum, other derivatives to facilitate plant growth and/or balance soil pH or combination thereof.

The pyrolysis reactor may be optimized by adjusting parameters based on the monitoring of the biochar composition, exhaust gas composition and biomass composition. To optimize the pyrolysis reactions in the reactor, adjustments may be made to the temperature of the heat source, oxygen concentration in the pyrolysis reactor, the intensity of the blower or inert gas source and residence time. Residence time may be decreased by increasing speed of travel of the pyrolytic auger and/or tractor pulling the pyrolytic system.

After the biochar is cooled, quenched and/or infused with nutrients, the cooling and quenching auger 234 may carry the processed biochar into the biochar handling system 235. The biochar handling system 235 may configured to control the application of biochar back into the soil, the depositing of biochar into a storage receptacle and the tracking and mapping of the amount of biochar being reintegrated back into the soil.

Figure 21B:
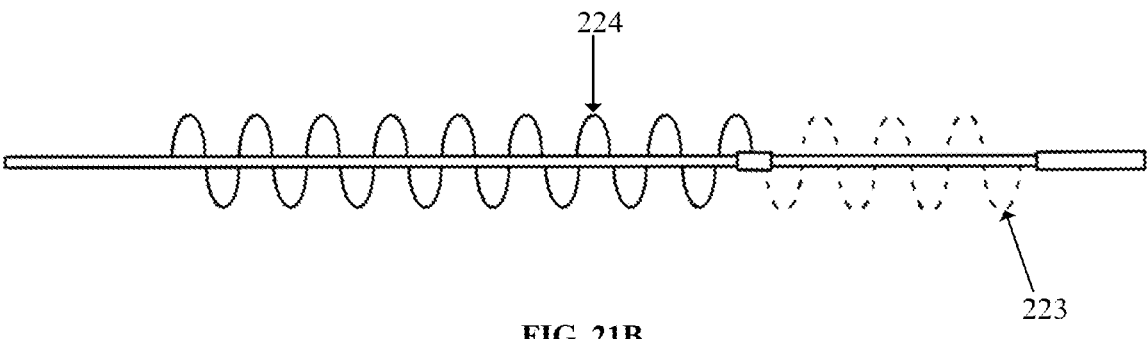
FIG. 21B illustrates an example of a pyrolytic auger in accordance with aspects of the present disclosure.
Figure 21C:
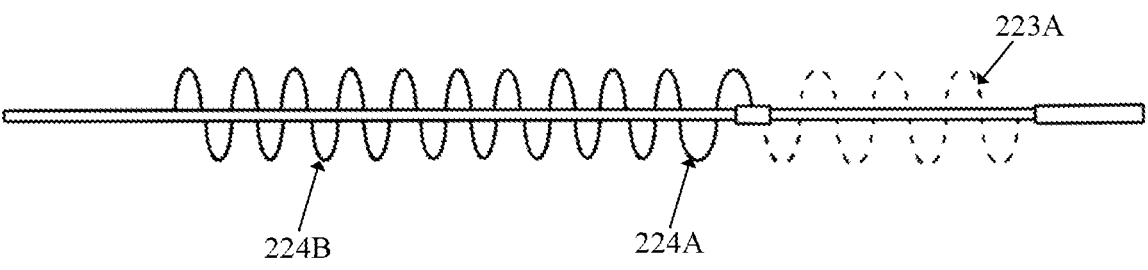
FIG. 21C illustrates an example of a pyrolytic auger in accordance with aspects of the present disclosure.
Figure 21D:
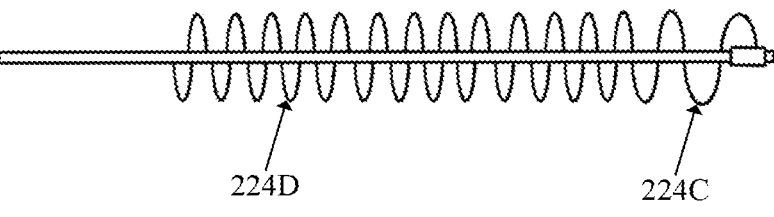
FIG. 21D illustrates an example of a pyrolytic auger in accordance with aspects of the present disclosure.

FIGS. 21B-D illustrate examples of pyrolytic augers in accordance with aspects of the present disclosure. FIG. 21B shows an example pyrolytic auger configured with a section of cut flights 223, which may be at a standard spacing. The cut flights 223 then transition to standard flights 224 for the remainder of the shafts length. FIG. 21C shows an example pyrolytic auger configured with cut and folded flights 223A, which may be at a standard spacing. The cut and folded flights 223A may transition to a standard flight 224A, wherein the transition occurs over a predetermined length, and wherein the transition narrow the flight spacing from the standard spacing to one which is narrower than the standard spacing. In some embodiments, the spacing may be narrowed at a constant or variable rate over the entire length of the auger shaft. In other embodiments, the narrowing is restricted to a transition region, with the remainder of the flights having the same but smaller flight spacing 224B. In some embodiments, the transition may be from a standard flight spacing to a spacing that is between ¼ and ½ narrower. In other embodiments the narrowing of the flights may be by ⅓. FIG. 21D shows an example pyrolytic auger configured with a flight transition portion 224C of the pyrolytic auger, wherein the flight transition portion 224C transitions the flights from a standard spacing to a double flight spacing 224D.

Figure 21E:
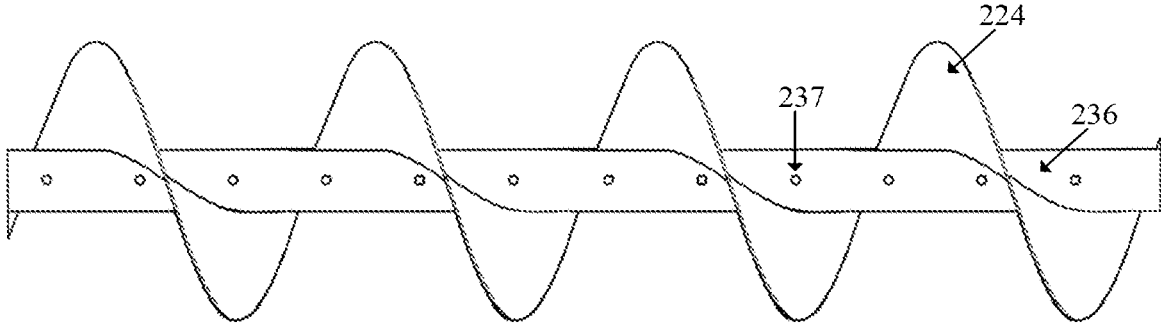
FIG. 21E illustrates an example of a pyrolytic auger with a hollow shaft in accordance with aspects of the present disclosure.
Figure 21F:
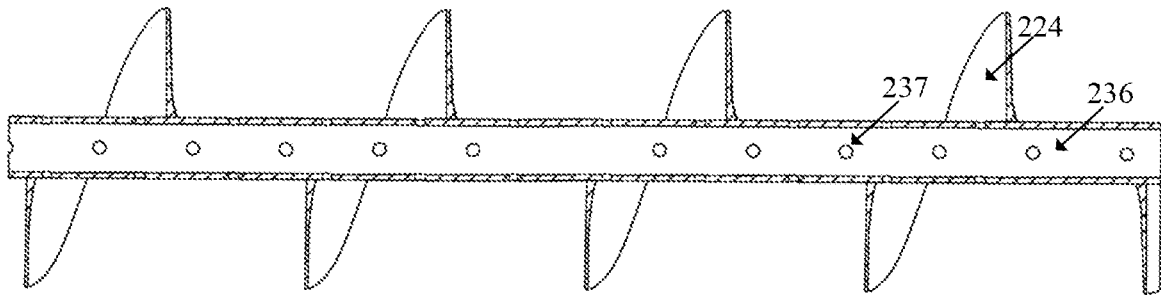
FIG. 21F illustrates an example of a pyrolytic auger with a hollow shaft in accordance with aspects of the present disclosure.

FIGS. 21E and 21F illustrate an example of a pyrolytic auger with a hollow shaft in accordance with aspects of the present disclosure. The pyrolytic auger shaft 222 of FIG. 21A may be replaced or used in conjunction with the hollow pyrolytic auger shaft 236 of FIGS. 21E and 21F. The hollow pyrolytic auger shaft 236 may comprise a plurality of injection holes 237. Exhaust gas, inert gas, atmospheric gas, steam or combination thereof may be injected into the pyrolytic reactor area of the system to adjust properties and characteristics of the pyrolysis reaction, the produced biochar and the exhaust gases generated. FIG. 21F shows a bisected view of the hollow pyrolytic auger shaft 236.

FIGS. 22A-22F illustrates an example of a towable biochar production system and pyrolysis reactor in accordance with aspects of the present disclosure. The trailer based biochar system 240 may comprise a trailer hitch 241 and a trailer bed 242. Mounted onto the trailer bed 240 may be a biomass intake 243, pyrolytic auger encasement 244, exhaust and biochar transfer unit 245, quenching auger assembly 246, biochar handling system 247, collection receptacle mount 248, biochar collection receptacle 249, water tank 250, hopper 251 and liquid nutrient tanks 253.

The hopper 251 may receive preprocessed biomass from a forage harvester or other harvesting unit. In some embodiments, the hopper 251 may be configured to determine the moisture content of the biomass, and based on the determination, perform a drying operation on the biomass if the moisture level is above a predetermined threshold. The hopper 251 may direct the biomass into a biomass intake 243. The biomass intake 243 feeds the dried biomass into the pyrolytic auger encasement 244. A pyrolytic auger is rotated to transfer the biomass into a pyrolytic reaction region within the encasement. After the pyrolysis reaction has been completed in the encasement, the exhaust and biochar transfer unit 245 may direct the generated exhaust gas into the atmosphere directly or through a chimney with a catalytic combustor. The transfer unit 245 may then also transfer the hot biochar into a quenching auger assembly 246 to reduce the temperature of the biochar. Within the quenching auger assembly 246, water and liquid nutrients from water tank 250 and liquid nutrient tanks 253 may be integrated into the biochar to reduce the temperature of the biochar at the same time as applying nutrients and soil amendments.

The biochar handling system 247 may be configured to distribute and integrate the receive postprocessed biochar into the soil or it may be configured to transfer it into a collection receptacle 249. The collection receptacle may be mounted to the trailer by a collection receptacle mount 248.

Figures 22A, 22B:
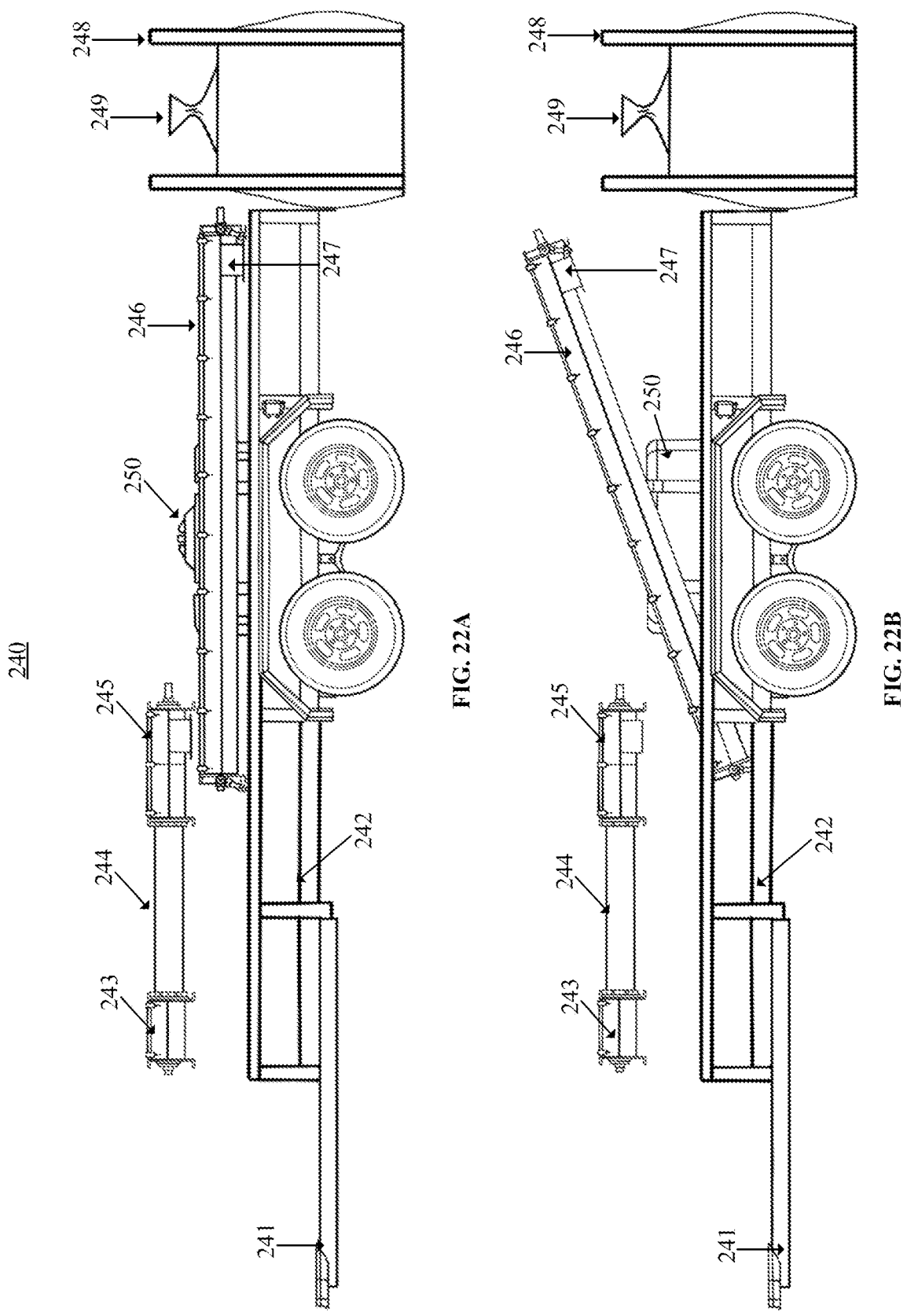
FIG. 22A illustrates an example of a towable biochar production system and pyrolysis reactor in accordance with aspects of the present disclosure.
FIG. 22B illustrates an example of a towable biochar production system and pyrolysis reactor in accordance with aspects of the present disclosure.
Figures 22C, 22D:
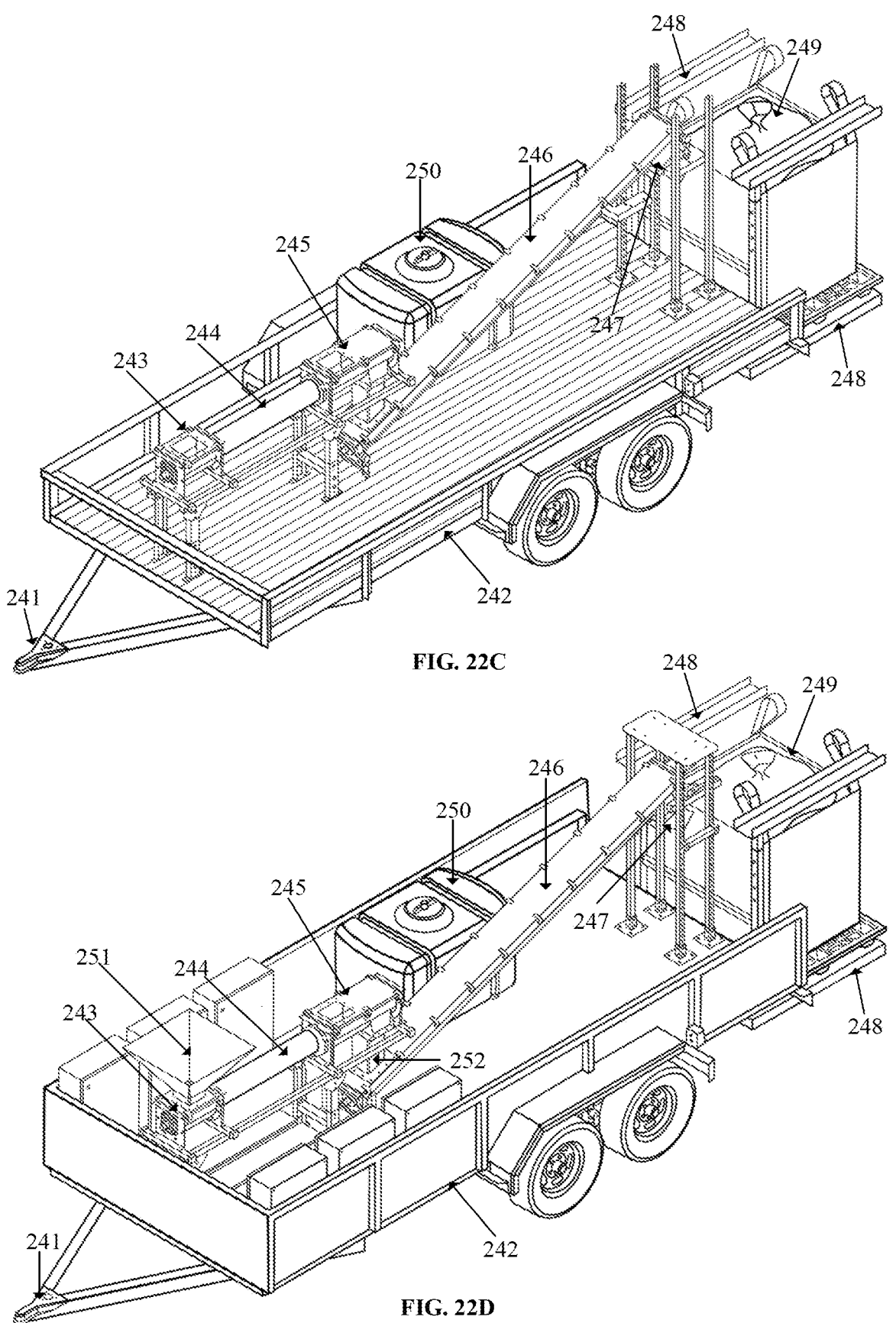
FIG. 22C illustrates an example of a towable biochar production system and pyrolysis reactor in accordance with aspects of the present disclosure.
FIG. 22D illustrates an example of a towable biochar production system and pyrolysis reactor in accordance with aspects of the present disclosure.
Figures 22E, 22F:
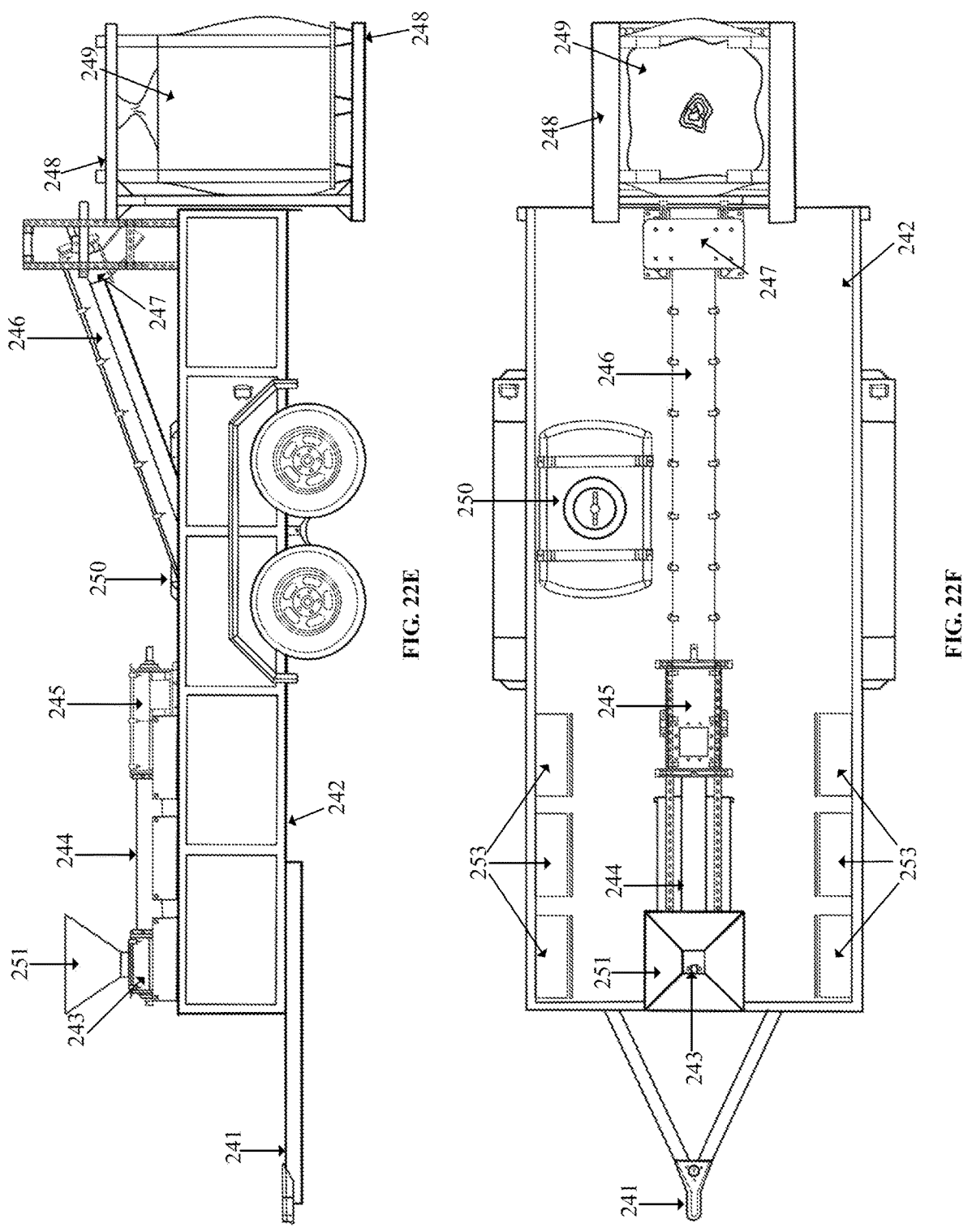
FIG. 22E illustrates an example of a towable biochar production system and pyrolysis reactor in accordance with aspects of the present disclosure.
FIG. 22F illustrates an example of a towable biochar production system and pyrolysis reactor in accordance with aspects of the present disclosure.
Figures 22G, 22H:
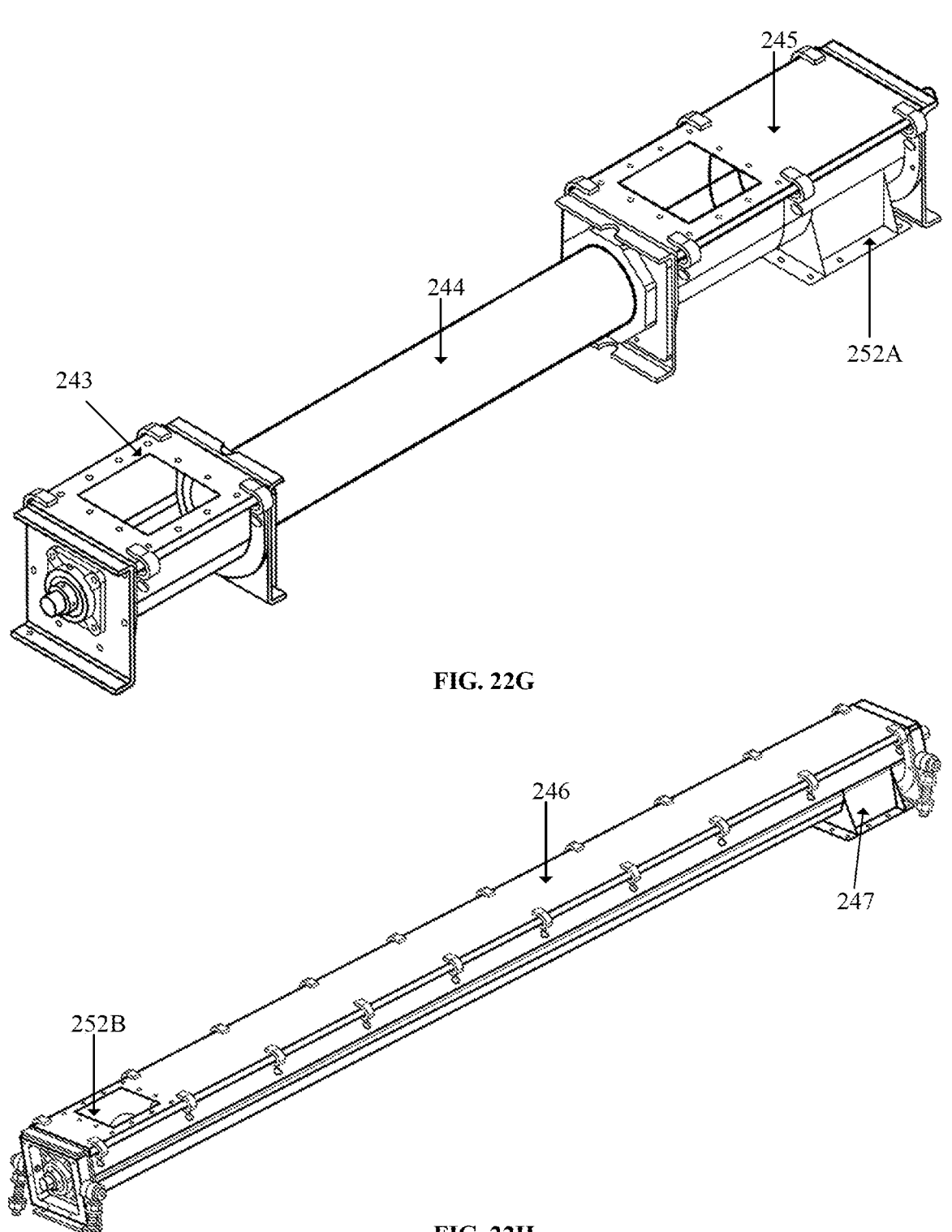
FIG. 22G illustrates an example of a thermally insulated enclosure of a pyrolytic auger and pyrolysis system in accordance with aspects of the present disclosure.
FIG. 22H illustrates an example of a cooling system with a quenching auger in accordance with aspects of the present disclosure.

FIGS. 22G-22H illustrate a thermally insulated enclosure of a pyrolytic auger, a cooling system of a quenching auger and the connecting of the two structures in accordance with aspects of the present disclosure.

The connection of the two components is accomplished through by way of a pyrolysis enclosure coupler 252A and a cooling system coupler 252B. The coupling allows the exhaust and biochar transfer unit 245 to directly transfer the biochar into the quenching auger assembly 246 for postprocessing of the biochar.

Figure 22I:
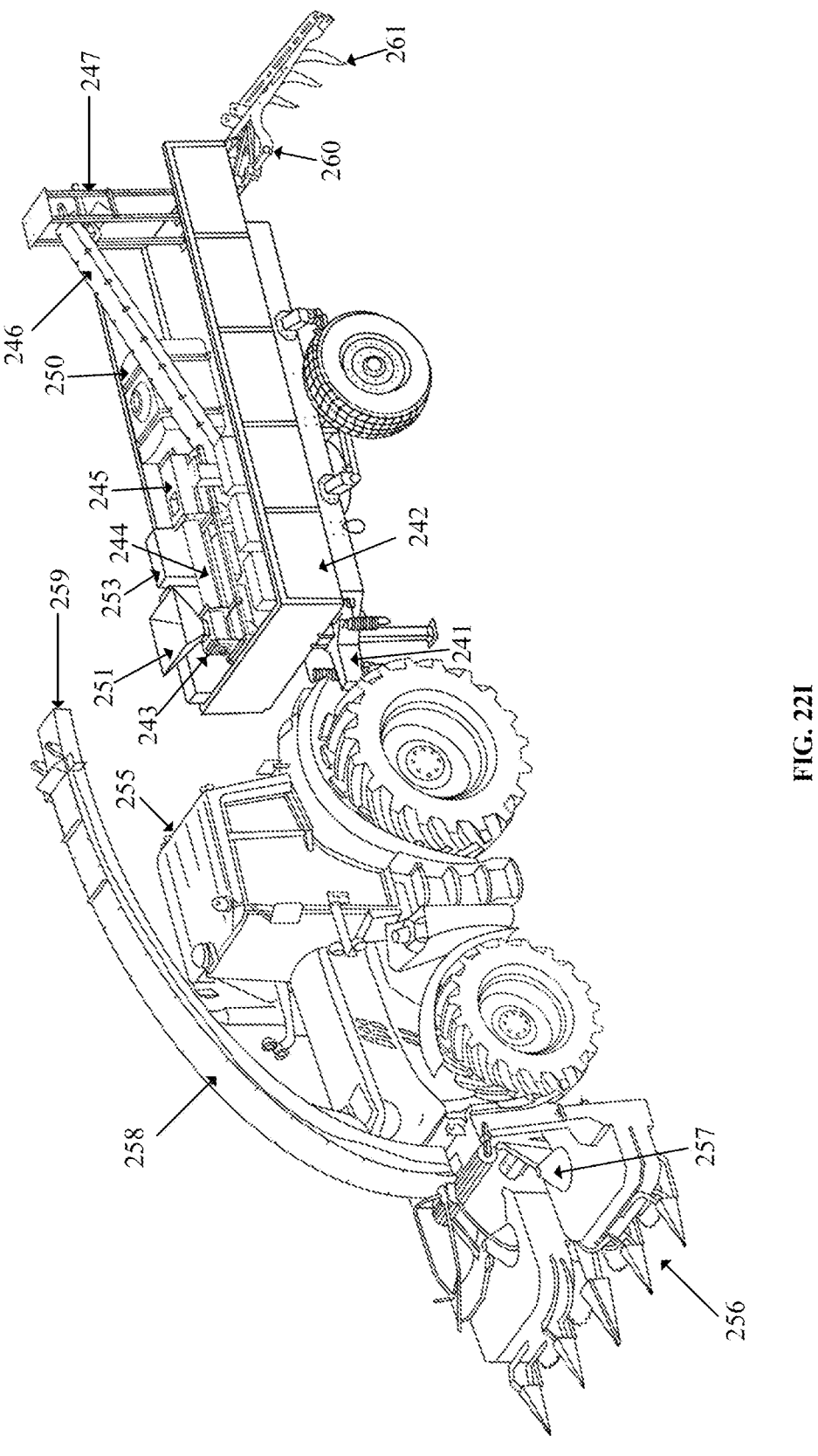
FIG. 22I illustrates an example of a biochar production system and pyrolysis reactor being towed by a tractor with an attached frontal forage harvester in accordance with aspects of the present disclosure

FIG. 22I illustrates an example of a biochar production system and pyrolysis reactor being towed by a tractor with an attached frontal forage harvester in accordance with aspects of the present disclosure. The biochar system of FIG. 22I is similar to that of FIGS. 22A-22F. However, in FIG. 22I, the biochar system 240 is shown as being attached to a mobile platform 255. The mobile platform may be autonomous, semi-autonomous and human supervised or human operated tractor. The mobile platform may be any tractor or vehicle capable of hauling the biochar trailer. The mobile platform may be attached to the trailer at trailer hitch 241.

A forage harvester 256 may be mounted to the front of the mobile platform 255. The forage harvester 256 may also be mounted at other positions on the mobile platform 255. Front mounted sensor array 257 may be configured to analyze the biomass in front of the harvester. The front mounted sensor array 257 may be mounted directly on the forage harvester 256 or onto the mobile platform 255.

The biomass conveyor system 258 may receive preprocessed biomass from the forage harvester 256. The conveyor system may further preprocess the biomass as it transfers the biomass from the forage harvester 256 to the hopper 251. In some embodiments, the further processing in the conveyor system 258 may comprise further cutting, chopping or milling of the biomass. The further processing may also include heating and drying of the biomass during the transfer of the biomass, reducing the amount of additional processing needed at the hopper 251 and the biomass intake 243. The conveyor system may use a conveyor belt, auger, forced air, suction or combination thereof to perform the transferring of the biomass into the auger.

The biomass transfer unit 259 may directly couple the conveyor system 258 to the hopper 251. In some embodiments, one or more additional units may be positioned between the transfer unit 259 and the conveyor system 258 as well as between the transfer unit 259 and the hopper 251. In some embodiments, the transfer unit 259 may make the transfer of biomass in open air, such as by dropping the biomass into a hopper while being separated from the hopper by open air.

Biochar spreading attachment 260, may comprise one or more sensor arrays to measure the quality, composition and mass of the biochar being handled. The sensor may also analyze the application density of the biochar. The biochar spreading attachment 260 may also comprise components configured to produce an even application of biochar to the soil. The spreading attachment 260 may work in conjunction with the biochar plowing attachment 261 to evenly distribute and integrate the biochar into the soil.

The biochar plowing attachment 261, comprise plowshares, moldboards and coulters. The plowing attachment 261 may adjust the depth and spacing of the component based on the distribution pattern, density and rate of the spreading attachment 260. Other raking and tilling implements may also be attached to the mobile platform 255 and/or the trailer itself. The biochar spreading attachment 260 and the biochar plowing attachment 261 may be replaced or substituted by these other raking and tilling implements, or may be removed, uninstalled or not installed in the first place.

Figure 23:
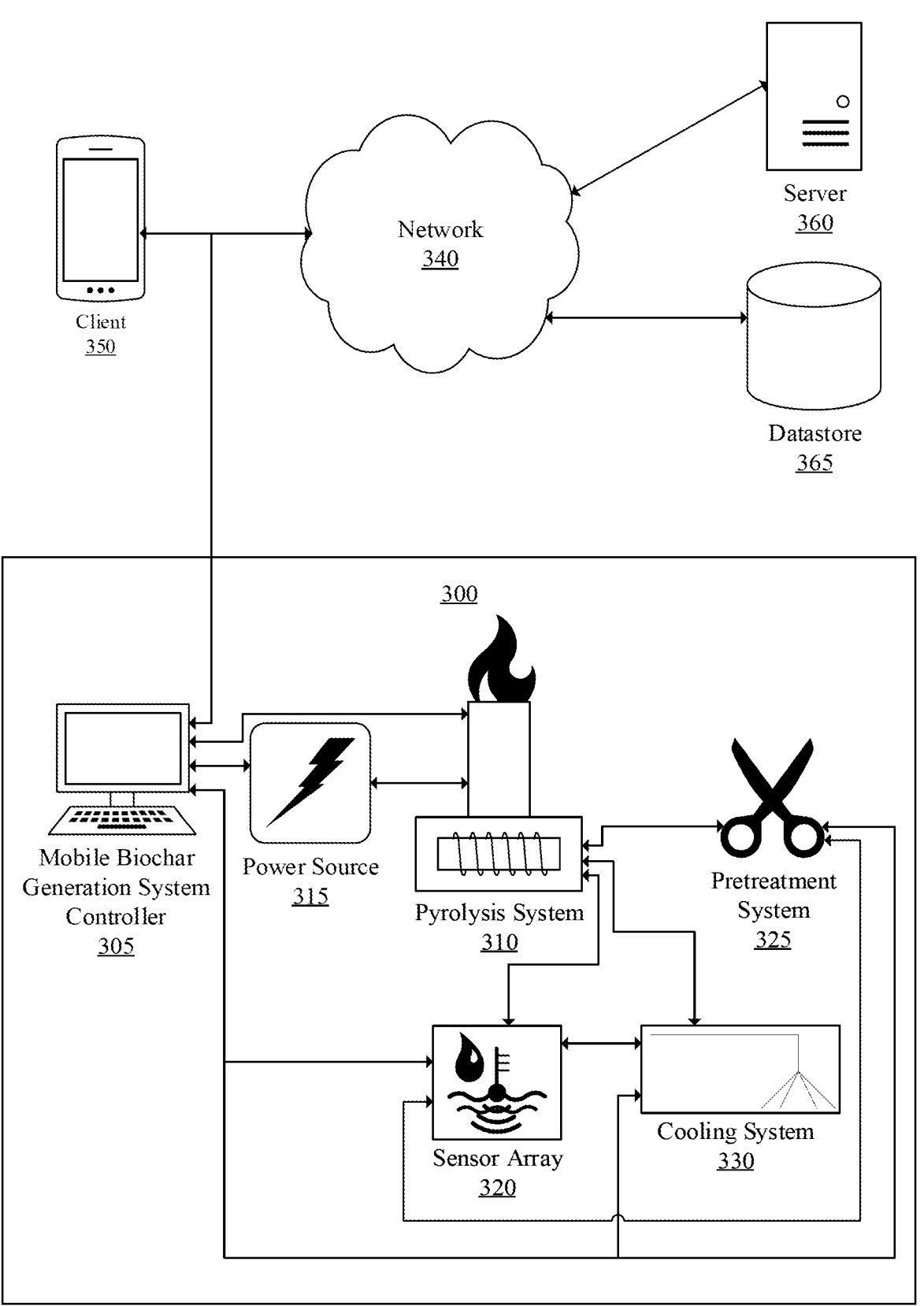
FIG. 23 illustrates an example of a mobile biochar generation system in accordance with aspects of the present disclosure.

FIG. 23 illustrates an example of a Mobile Biochar Generation System (MBGS) 300 in accordance with aspects of the present disclosure. Mobile biochar generation system 300 may comprise an MBGS controller 305, pyrolysis system 310, power source 315, sensor array 320, pretreatment system 325 and cooling system 330.

The MBGS Controller 305 may coordinate the operation of the pyrolysis system 310, pretreatment system 325 and cooling system 330 based on the information received from sensor array 320. The MBGS controller 305 may also control navigation of a tractor integrated with the system to facilitate maneuvering of the system over a field. The MBGS controller 305 may also be configured to control harvesting equipment and equipment for the distribution and integration of the biochar into the soil of the field.

Power source 315 may be used in the operation of the controller 305, as well as that of the pyrolysis system 310, pretreatment system 325 and cooling system 330. The power source 315 may battery or generator based.

The MBGS 300 may communicate with client 350, server 360 and datastore 365 over network 340. Client device 350 may be a personal computer, handheld computing device, smartphone or other user operated devices that can communicate with the MBGS 300, either directly or over network 340. Server 360 may be any computing device(s) capable of performing the methods and processes described in this disclosure. Datastore 365 may store data generated from the MBGS, including readings from sensor arrays, analytical results of the biomass, biochar, exhaust gas or any other raw or processed information produced as a result of the operation of the system.

Figure 24A:
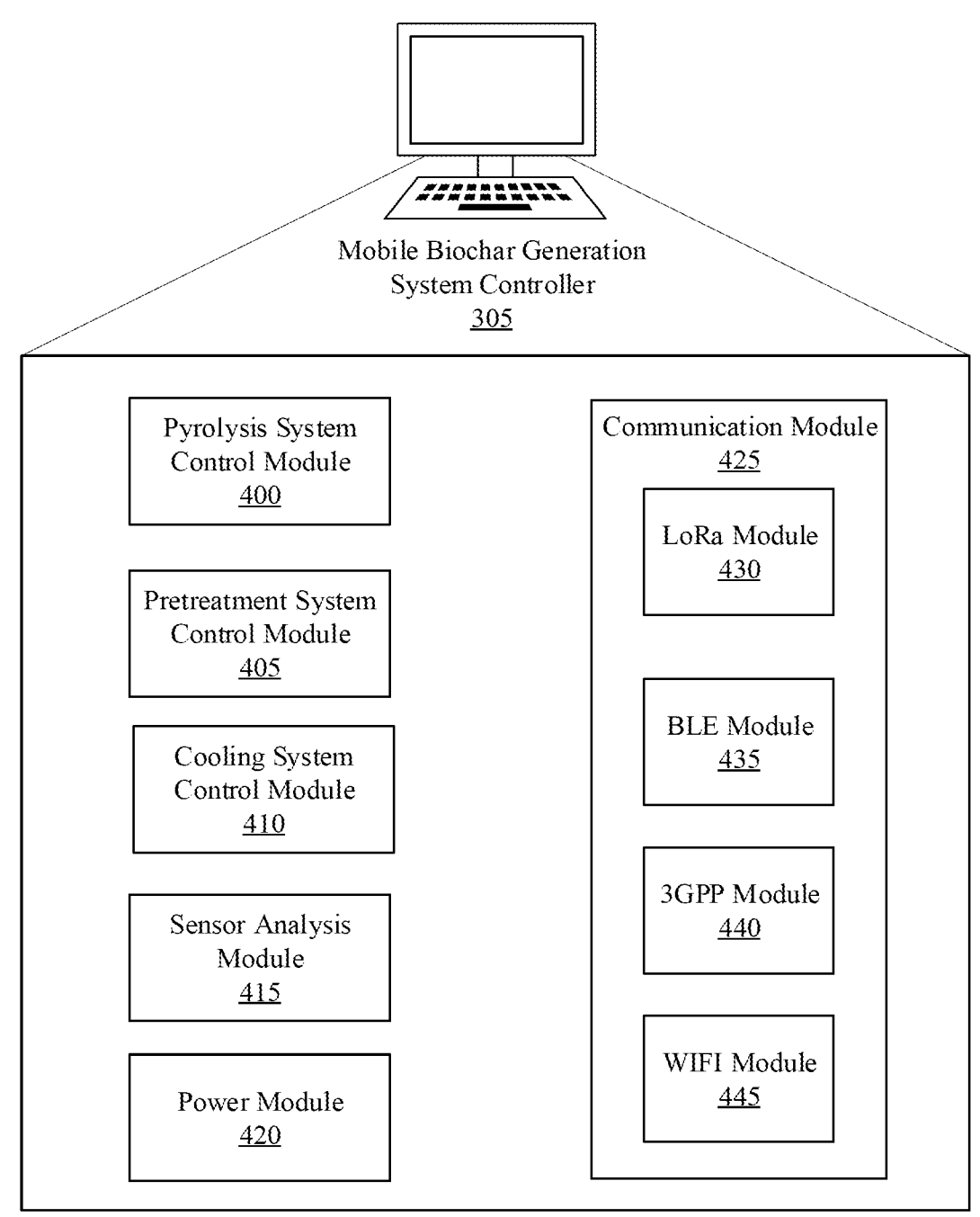
FIG. 24A illustrates an example of a biochar generation system controller in accordance with aspects of the present disclosure.

FIG. 24A illustrates an example of MBGS controller in accordance with aspects of the present disclosure. The MBGS controller 305 may comprise a pyrolysis system control module 400, pretreatment system control module 405, cooling system control module 410, sensor analysis module 415, power module 420, and a communication module 425.

Pyrolysis system control module 400 may control all aspects of the pyrolytic reactor and pyrolytic auger. The controller may be configured to adjust gas injection, temperature and residence time within the pyrolytic reactor. Pretreatment system control module 405 may be used to control the harvesting, chopping, conveyance and drying of the biomass. The cooling system control module 410 may control the operation of blowers, water sprayers, peltier coolers, refrigeration units and nutrient integration into the biochar. The sensor analysis module 415 may be configured to determine composition and other characteristics of the biomass before harvesting, during harvesting, during preprocessing and during pyrolysis. The sensor analysis module 415 may also be configured to determine composition and other characteristics of the biochar and exhaust gas during pyrolysis, after pyrolysis, during quenching and cooling, after nutrient infusion, and after distribution and integration of the biochar into the soil.

Communication module 425 may comprise a LoRa module 430, BLE module 435, 3GPP module 440 and WIFI module 445.

Figure 24B:
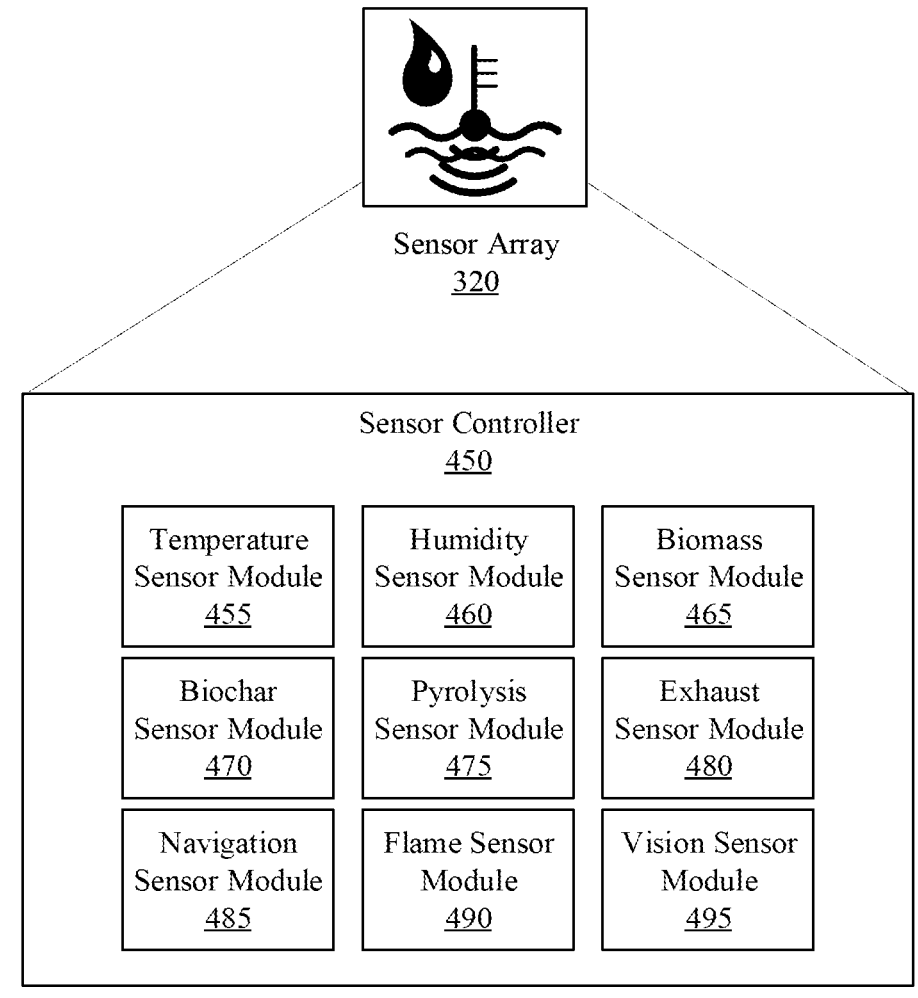
FIG. 24B illustrates an example of a sensor array controller in accordance with aspects of the present disclosure.

FIG. 24B illustrates an example of a sensor array 320 in accordance with aspects of the present disclosure. Sensor array 320 may comprise a sensor controller 450, a temperature sensor module 455, a humidity sensor module 460, biomass sensor module 465, a biochar sensor module 470, a pyrolysis sensor module 475, an exhaust sensor module 480, a navigation sensor module 485, a flame sensor module 490 and a vision sensor module 495.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Figure 25:
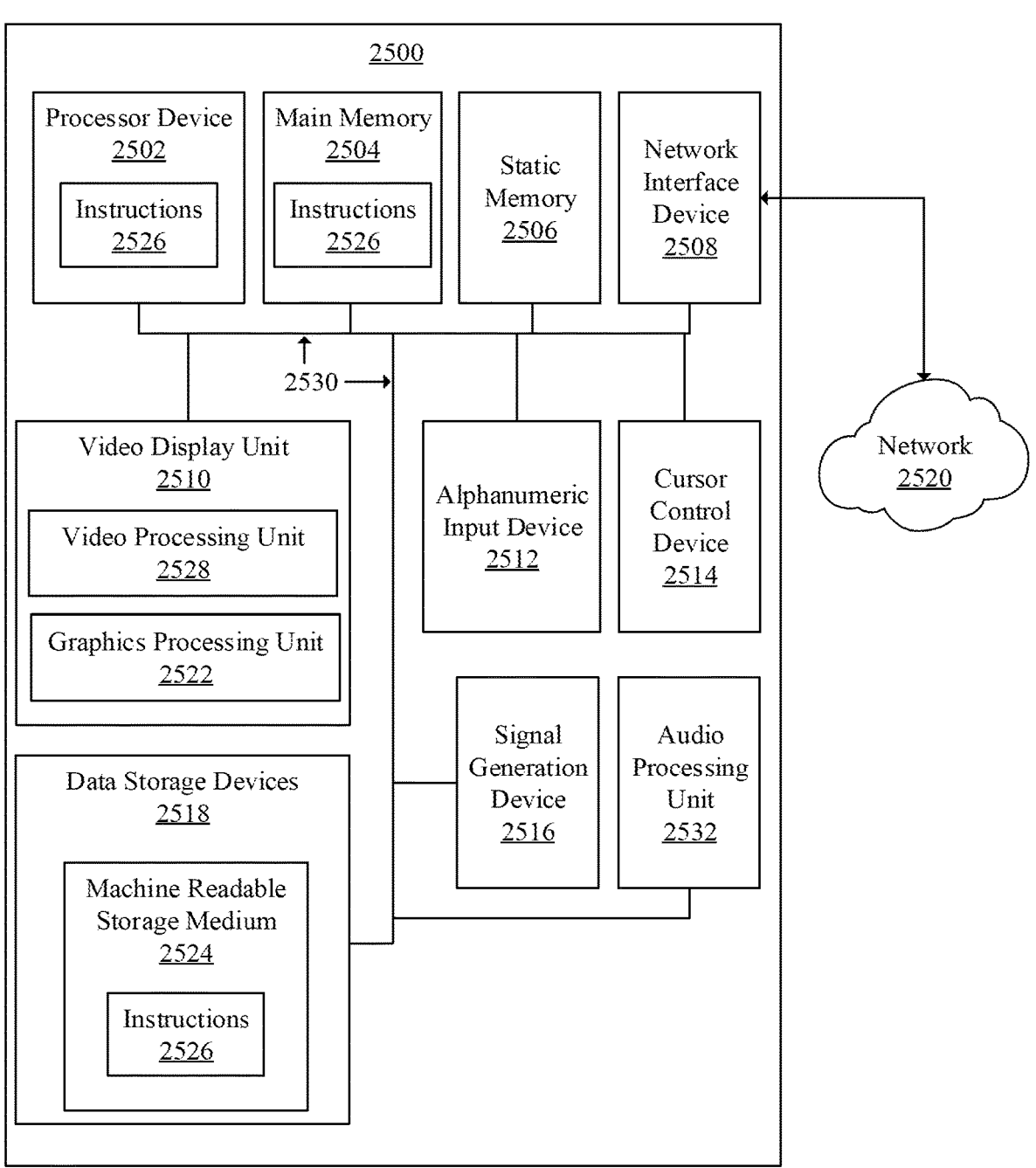
FIG. 25 is a diagram illustrating an exemplary computer that may perform processing in some embodiments and in accordance with aspects of the present disclosure.

FIG. 25 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 2500 includes a processing device 2502, a main memory 2504 (e.g., read-only memory (ROM), flash memory, dynamic random access memory (DRAM) such as synchronous DRAM (SDRAM) or Rambus DRAM (RDRAM), etc.), a static memory 2506 (e.g., flash memory, static random access memory (SRAM), etc.), and a data storage device 2518, which communicate with each other via a bus 2530.

Processing device 2502 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 2502 may also be one or more special-purpose processing devices such as an application specific integrated circuit (ASIC), a field programmable gate array (FPGA), a digital signal processor (DSP), network processor, or the like. The processing device 2502 is configured to execute instructions 2526 for performing the operations and steps discussed herein.

The computer system 2500 may further include a network interface device 2508 to communicate over the network 2520. The computer system 2500 also may include a video display unit 2510 (e.g., a liquid crystal display (LCD) or a cathode ray tube (CRT)), an alphanumeric input device 2512 (e.g., a keyboard), a cursor control device 2514 (e.g., a mouse), a graphics processing unit 2522, a signal generation device 2516 (e.g., a speaker), graphics processing unit 2522, video processing unit 2528, and audio processing unit 2532.

The data storage device 2518 may include a machine-readable storage medium 2524 (also known as a computer-readable medium) on which is stored one or more sets of instructions or software 2526 embodying any one or more of the methodologies or functions described herein. The instructions 2526 may also reside, completely or at least partially, within the main memory 2504 and/or within the processing device 2502 during execution thereof by the computer system 2500, the main memory 2504 and the processing device 2502 also constituting machine-readable storage media.

In one implementation, the instructions 2526 include instructions to implement functionality corresponding to the components of a device to perform the disclosure herein. While the machine-readable storage medium 2524 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

FIG. 26A is a flow chart illustrating the operation of the mobile biochar generation unit 2600 in accordance with some embodiments.

At step 2601, the system may control, by a system controller, a mobile biochar generation system. At step 2602, the system may determine an optimal path for the mobile biochar generation system to traverse. At step 2603, the system may operate a harvesting unit to collect and harvest biomass feedstock to be pyrolyzed. At step 2604, the system may monitor, using a first sensor array, the harvested biomass feedstock. At step 2605, the system may load, by a pyrolyzing auger, the harvested biomass feedstock into a pyrolytic reactor. At step 2606, the system may pyrolyze, in the pyrolytic reactor, the harvested biomass feedstock to generate biochar and exhaust gas. At step 2607, the system may monitor, using the second sensor array, the biochar and the exhaust gas. At step 2608, the system may postprocess the biochar based on the monitoring of the feedstock, the biochar and exhaust gas. At step 2609, the system may determine optimization adjustments of one or more operating parameters of the pyrolytic reactor based on the monitoring of the biochar and exhaust gas. At step 2610, the system may make adjustments of the one or more operating parameters of the pyrolytic reactor based on the determined optimization adjustments. The system may then continue to pyrolyze the harvested biomass feedstock with the adjusted operating parameters.

FIG. 26B is a flow chart illustrating the postprocessing of biochar 2608 in the mobile biochar generation unit in accordance with some embodiments.

At step 2611, the system may determine the composition of the biochar and exhaust gas. At step 2612, the system may cool, in a cooling and quenching auger assembly, the biochar to a predetermined temperature. At step 213, the system may infuse the biochar with nutrients or soil amendments. At step 2614, the system may handle, by a biochar handling unit, the infused biochar, wherein the handling comprises application of the infused biochar into a soil region. At step 2615, the system may monitor, by a third sensor array, the infused biochar and determine the composition and mass of the infused biochar. At step 2616, the system may map the application of the infused biochar to a corresponding coordinate system of a piece of land. At step 2617, the system may store the mapping of the infused biochar application.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. An apparatus for in-field production of biomass into biochar, the apparatus comprising:
   a mobile biochar generation system, wherein the mobile biochar generation system comprises:
   a mobile platform, wherein the mobile platform comprises a tractor unit;
   a trailer unit, wherein the trailer unit comprises a trailer bed and a trailer hitch, wherein the trailer hitch connects the mobile platform with the trailer unit;
   a harvesting unit, wherein the harvesting unit comprises:
      a first sensor array, configured to monitor the biomass being harvested;
      a forage harvester, wherein the forage harvester is mounted to the front of the mobile platform;
      a biomass intake unit, wherein the biomass intake unit transfers the harvested biomass to a conveyor unit;
      wherein the conveyer unit transfers the harvested biomass from the forage harvester to a biomass transfer unit; and
      wherein the biomass transfer unit deposits the harvested biomass to a pyrolytic system;
   the pyrolytic system comprising:
   a biomass intake unit, wherein the biomass intake unit comprises a hopper unit, wherein the biomass intake unit receives harvested biomass into the hopper unit;
   a pyrolytic reactor unit, wherein the pyrolytic reactor unit comprises:
   a pyrolysis control unit, wherein the pyrolysis control unit controls temperature and gas injection;
   a pyrolytic auger, wherein the pyrolytic reactor comprises:
      a first portion with one or more cut flights; and
      a second portion configured to transition from a first flight spacing to a second flight spacing;
   a thermally insulated reactor enclosure;
   an exhaust transfer unit;
   a biochar transfer unit;
   a heating unit; and a second sensor array;

an exhaust handling unit, wherein the exhaust handling unit comprises:

an exhaust coupling unit;

a chimney unit;

a blower unit; and a catalytic combustor;

a cooling unit, wherein the cooling unit comprises:

a quenching auger assembly, wherein the quenching auger assembly further comprises:

one or more active cooling components, wherein the active cooling components comprise blowers and water sprinklers; and one or more passive cooling components, wherein the passive cooling components comprise heat sinks, peltier coolers and refrigeration units;

one or more water storage units;

one or more nutrient storage units; and a nutrient integration unit;

a biochar handling system, wherein the biochar handling system comprises:

a biochar spreading unit;

a biochar plowing unit; and a third sensor array.

2. The apparatus of claim 1, wherein the pyrolytic reactor unit generates biochar and exhaust gas from the harvested biomass.

3. The apparatus of claim 2, wherein the nutrient integration unit infuses the biochar with nutrients or soil amendments to produce infused biochar.

4. The apparatus of claim 3, wherein the biochar handling system integrates the infused biochar into a soil region.

5. The apparatus of claim 4, wherein the biochar handling system maps the amount of the infused biochar integrated into the soil to a corresponding coordinate system of a piece of land.

6. The apparatus of claim 1, wherein the pyrolysis control unit optimizes pyrolyzing in the pyrolytic reactor by adjusting one or more operating parameters of the pyrolytic reactor, wherein the one or more operating parameters are determined based on a determined composition of biochar and exhaust gas.

7. A biochar production system, the system comprising:

a mobile platform configured to drive across open land containing biomass feedstock;

a trailer coupled to and configured to be moved by the mobile platform;

a harvesting unit coupled to the mobile platform, wherein the harvesting unit is configured to harvest biomass feedstock from the open land; and a pyrolytic unit located on the trailer, wherein the pyrolytic unit is configured to receive the biomass feedstock harvested by the harvesting unit and convert via pyrolysis the harvested biomass feedstock into biochar and exhaust gas;

wherein the pyrolytic unit comprises:

a sensor array configured to monitor temperature, gas composition, and biochar carbon content; and a control unit configured to automatically adjust one or more operating parameters of the pyrolytic unit based on data from the sensor array to produce a target biochar composition.

8. The system of claim 7, further comprising:

a nutrient integration unit, wherein the nutrient integration unit is configured to infuse the biochar with nutrients to produce infused biochar, wherein the nutrients comprise Nitrogen, Phosphorous, Potassium, Calcium, Magnesium, Sulfur, Iron, Manganese, Copper, Zinc, Boron, Molybdenum, and other derivatives thereof that facilitate plant growth and/or balance soil pH.

9. The system of claim 8, further comprising:

a biochar handling system comprising:

a biochar spreading unit;

a biochar plowing attachment; and one or more sensor arrays that measure a composition and a mass of biochar being handled by the biochar handling system;

wherein the biochar handling system is configured to integrate the infused biochar into a soil region at or proximate the open land.

10. The system of claim 9, wherein the biochar handling system includes the biochar spreading unit configured to control the amount and density of the infused biochar applied to the soil region and the biochar plowing unit configured to control integration of the infused biochar into the soil region.

11. The system of claim 9, wherein the biochar handling system is further configured to map and store the amount of the infused biochar being integrated into the soil region to a corresponding coordinate system.

12. The system of claim 7, further comprising:

a remote server; and a control unit configured to communicate with a remote server via a network connection, wherein the remote server is configured to analyze sensor data obtained by the sensor array and transmit updated optimization parameters to the control unit for subsequent field operations performed by the system.

13. The system of claim 12, wherein the mobile platform includes one or more sensors and one or more processors, and wherein the mobile platform is configured to determine automatically an optimal path for the mobile platform to drive across the open land, wherein the mobile platform utilizes onboard cameras and a computer vision process to identify a presence of rows in the open land and to identify a presence of any obstacles that may impede the movement of the mobile platform.

14. The system of claim 7, wherein the pyrolytic unit is configured to determine a composition of biochar and exhaust gas produced in the pyrolytic unit.

15. The system of claim 14, wherein the pyrolytic unit comprises:

a first portion with one or more cut flights;

a second portion configured to transition from a first flight spacing to a second flight spacing;

a thermally insulated reactor enclosure;

an exhaust transfer unit;

a biochar transfer unit;

a heating unit; and an exhaust handling unit, wherein the exhaust handling unit comprises:

an exhaust coupling unit;

a chimney unit;

a blower unit; and a catalytic combustor;

wherein the pyrolytic unit is further configured to optimize the pyrolysis performed therein by adjusting one or more operating parameters based on the determined composition of biochar and exhaust gas.

16. The system of claim 7, wherein the system is configured to adjust one or more pyrolysis process parameters to produce a desired amount of one or more pyrolysis products.

17. The system of claim 16, wherein the one or more pyrolysis products include biochar, pyrolysis gas, pyrolysis oil, or any combination thereof.

18. The system of claim 7, further comprising:

a harvesting assembly for cutting and feeding the biomass feedstock directly into the pyrolytic unit, wherein the pyrolytic unit comprises a pyrolytic reactor; and a pyrolysis control system including sensors and controllers configured to adjust temperature, feed rate, and gas flow parameters in real time based on monitored composition data; and a biochar handling system configured to cool the biochar.

19. The system of claim 7, further comprising:

a hopper;

a biomass intake; and a pyrolytic auger;

wherein the harvesting unit includes a forage harvester located in front of or behind the mobile platform that feeds the biomass feedstock into the hopper;

wherein the hopper directs the fed biomass stock into the biomass intake;

wherein the biomass intake directs the fed biomass feedstock to the pyrolytic auger; and wherein the pyrolytic auger directs the biomass feedstock into a pyrolytic reaction region of the pyrolytic unit.

20. The system of claim 8, wherein the system is configured to monitor the harvested biomass feedstock to track and characterize one or more characteristics or properties of the harvested biomass feedstock.

21. The system of claim 7, wherein the pyrolytic reactor is configured to operate in a stationary mode, where the pyrolytic unit receives the biomass feedstock delivered from external feedstock sources and processing the biomass feedstock into the biochar at a fixed location.

22. The system of claim 7, wherein the mobile platform and the trailer are configured as a single self-propelled unit.

\* \* \* \* \*